(12) United States Patent
Guevara-Torres et al.

(10) Patent No.: US 11,337,604 B2
(45) Date of Patent: May 24, 2022

(54) IN VIVO OBJECT IDENTIFICATION, COUNTING, AND IMAGING BASED ON LIGHT BACKSCATTERED FROM A PLANE BEHIND THE OBJECT

(71) Applicant: University of Rochester, Rochester, NY (US)

(72) Inventors: Raul Andres Guevara-Torres, Rochester, NY (US); Jesse Schallek, Rush, NY (US); Aby Joseph, Rochester, NY (US)

(73) Assignee: University of Rochester, Rochester, NY (US)

( * ) Notice: Subject to any disclaimer, the term of this patent is extended or adjusted under 35 U.S.C. 154(b) by 160 days.

(21) Appl. No.: 16/660,312

(22) Filed: Oct. 22, 2019

(65) Prior Publication Data

US 2020/0121182 A1    Apr. 23, 2020

Related U.S. Application Data

(63) Continuation-in-part of application No. 16/205,925, filed on Nov. 30, 2018, now Pat. No. 11,185,222.

(60) Provisional application No. 62/749,394, filed on Oct. 23, 2018.

(51) Int. Cl.
   *A61B 3/14* (2006.01)
   *A61B 3/10* (2006.01)
   *A61B 3/00* (2006.01)
   *A61B 3/12* (2006.01)

(52) U.S. Cl.
   CPC .......... *A61B 3/1025* (2013.01); *A61B 3/0025* (2013.01); *A61B 3/1241* (2013.01); *A61B 3/14* (2013.01)

(58) Field of Classification Search
   CPC ... A61B 3/1025; A61B 3/0025; A61B 3/1241; A61B 3/14; A61B 3/12; A61B 3/13; A61B 5/14555; A61B 5/0082; G06K 9/209; G06K 9/00134
   USPC ........................................................ 351/206
   See application file for complete search history.

(56) References Cited

PUBLICATIONS

Artal, P., et al., "Odd aberrations and double-pass measurements of retinal image quality," 1995, J. Opt. Soc. Am. A, vol. 12, No. 2 (pp. 195-201).
Chui, T.Y.P., et al., "The use of forward scatter to improve retinal vascular imaging with an adaptive optics scanning laser ophthalmoscope," 2012, Biomedical Optics Express, vol. 3, No. 10 (pp. 2537-2549).
Elsner, A. E., et al., "Infrared Imaging of Sub-retinal Structures in the Human Ocular Fundus," 1996, Vision Res., vol. 36, No. 1 (pp. 191-205).
Geng, Y., et al., "Adaptive optics retinal imaging in the living mouse eye," 2012, Biomedical Optics Express, vol. 3, No. 4 (pp. 715-734).

(Continued)

*Primary Examiner* — Mahidere S Sahle
(74) *Attorney, Agent, or Firm* — Harris Beach PLLC

(57) ABSTRACT

A method to image an in vivo object in an eye includes illuminating an object in the eye by a light source; configuring one or more detectors to receive light from a conjugate plane behind a confocal plane of the object, the conjugate plane acting as a light screen; receiving at the one or more detectors a backscattered light from the light source which has been refracted at least in part by the object before being backscattered from the light screen to provide a detector data; and processing the detector data over a time period by a computer to generate information about the object.

20 Claims, 29 Drawing Sheets

(56) References Cited

PUBLICATIONS

Guevara-Torres, A., et al., "Label free measurement of retinal blood cell flux, velocity, hematocrit and capillary width in the living mouse eye," 2016, Biomedical Optics Express, vol. 7, No. 10 (pp. 4228-4249).

Rossi, E.A., et al., "Imaging individual neurons in the retinal ganglion cell layer of the living eye," 2017, PNAS, vol. 114, No. 3 (pp. 586-591).

Santamaria, J., et al., "Determination of the point-spread function of human eyes using a hybrid optical-digital method," 1987, J. Opt. Soc. Am. A, vol. 4, No. 6 (pp. 1109-1114).

Scoles, D., et al., "In Vivo Imaging of Human Cone Photoreceptor Inner Segments," 2014, IOVS, vol. 55, No. 7 (pp. 4244-4251).

Van Blokland, G.J., et al., "Intenstiy and Polarization of Light Scattered At Small Angles From the Human Fovea," 1986, Vision REs., vol. 26, No. 3 (pp. 485-494).

Sulai, Y.N., et al., "Visualization of retinal vascular structure and perfusion with a nonconfocal adaptive optics scanning light ophthalmoscope", Mar. 2014, J. Opt. Soc. Am. A, vol. 31, pp. 569-579.

Guevara-Torres, A., et al., "Imaging translucent cell bodies in the living mouse retina without contrast agents", May 2015, Biomedical Optics Express, vol. 6, pp. 2106-2119.

Borovoi, A. G., et al., "Scattering of Light by a Red Blood Cell," J. Biomed. Opt. 3, 364-372 (1998).

Chu, C. J., et al., Multimodal analysis of ocular inflammation using the endotoxin-induced uveitis mouse model. Disease Models and Mechanisms 9, 473-481 (2016).

Cuthbertson, R. A., et al., "Anatomy of the mouse retina. Endothelial cell-pericyte ratio and capillary distribution.," Invest. Ophthalmol. Vis. Sci. 27, 1659-1664 (1986).

Dubra, A., et al., "Registration of 2D Images from Fast Scanning Ophthalmic Instruments," in Biomedical Image Registration, Lecture Notes in Computer Science No. 6204 (Springer Berlin Heidelberg, 2010), pp. 60-71.

Elsner, A., et al., "Multiply scattered light tomography and confocal imaging: detecting neovascularization in age-related macular degeneration," Opt. Express 7, 95-106 (2000).

Fischer, M. D. G., et al., "Noninvasive, In Vivo Assessment of Mouse Retinal Structure Using Optical Coherence Tomography," PLoS ONE 4, e7507 (2009).

Ford, T. N., et al., "Phase-gradient microscopy in thick tissue with oblique back-illumination," Nat. Methods 9, 1195-1197 (2012).

Joannes, L., et. al., "Phase-shifting schlieren: high-resolution quantitative schlieren that uses the phase-shifting technique principle," Appl. Opt. 42, 5046-5053 (2003).

Josheph, A., et al., "Imaging single-cell blood flow in the smallest to largest vessels in the living retina." Elife 8, e45077 (2019).

Kim, K. H., et al., "Monitoring mouse retinal degeneration with high-resolution spectral-domain optical coherence tomography," J. Vis. 8, 17-17 (2008).

Kraats, J. V., et al., "The Pathways of Light Measured in Fundus Reflectometry," Vision Res. 36, 2229-2247 (1996).

Kreysing, M., et al., "Physical insight into light scattering by photoreceptor cell nuclei," Opt. Lett. 35, 2639-2641 (2010).

Marcos, S. et al. Vision science and adaptive optics, the state of the field. Vision Research 132, 3-33 (2017).

Marki, A., et al., Rolling neutrophils form tethers and slings under physiologic conditions in vivo. Journal of Leukocyte Biology 103, 67-70 (2018).

Remtulla, S., et al., "A schematic eye for the mouse, and comparisons with the rat," Vision Res. 25, 21-31 (1985).

Rosenbaum, J., et al., "Imaging Ocular Immune Responses" by Intravital Microscopy. Int Rev Immunol 21, 255-273 (2009).

Sapoznik, K. A., et al., "Enhanced retinal vasculature imaging with a rapidly configurable aperture," Biomed. Opt. Express 9, 1323-1333 (2018).

Uderhardt, S., et al., "Macrophages Cloak Tissue Microlesions to Prevent Neutrophil-Driven Inflammatory Damage". Cell 177, 541-555.e17 (2019).

Vohnsen, B., "Directional sensitivity of the retina: A layered scattering model of outer-segment photoreceptor pigments," Biomed. Opt. Express 5, 1569-1587 (2014).

Webb, R. H., et al., "Confocal scanning laser ophthalmoscope," Appl. Opt. 26, 1492-1499 (1987).

Woodfin, A., et al., "The junctional adhesion molecule JAM-C regulates polarized transendothelial migration of neutrophils in vivo". Nature immunology 12, 761-9 (2011).

PCT International Preliminary Report on Patentability for PCT/US 2019/05747 (7 pages).

FIG. 1
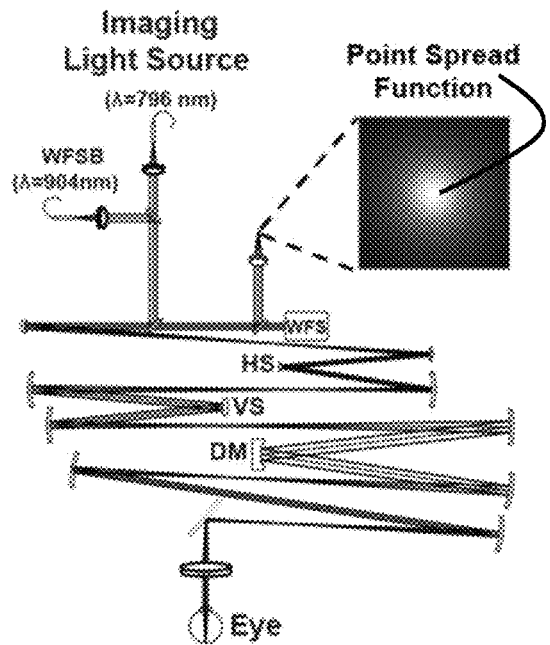
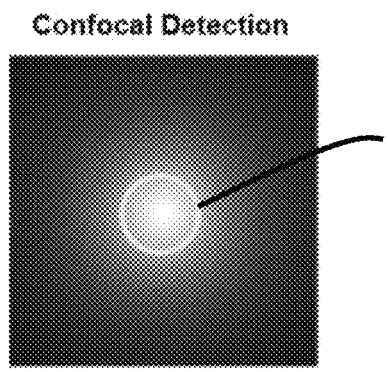
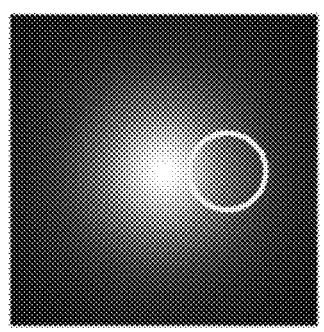 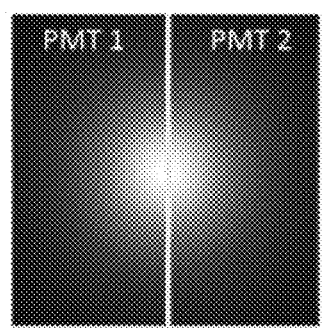
FIG. 2A
FIG. 2B   FIG. 2C

FIG. 3B Offset Detection

Ganglion Cell Image

Left Edge Bright

Ganglion Cell Image

Right Edge Dark

Detail of light path as it
Travels through the retina to a blood cell
And is reflected by a deeper screen

IN VIVO OBJECT IDENTIFICATION, COUNTING, AND IMAGING BASED ON LIGHT BACKSCATTERED FROM A PLANE BEHIND THE OBJECT

CROSS-REFERENCE TO RELATED APPLICATIONS

This application is a continuation-in-part (CIP) of and claims the benefit of copending U.S. patent application Ser. No. 16/205,925, LABEL-FREE CONTRAST ENHANCEMENT FOR TRANSLUCENT CELL IMAGING BY PURPOSEFULLY DISPLACING THE DETECTOR, filed Nov. 30, 2018, and U.S. Provisional Application No. 62/749,394, filed Oct. 23, 2018, BLOOD CELL IDENTIFICATION USING COMPARISONS OF SCATTER IN SINGLE AND DOUBLE PASS LIGHT IN THE LIVING RETINA the disclosure of which Applications are incorporated by reference herein in their entirety.

STATEMENT REGARDING FEDERALLY FUNDED RESEARCH OR DEVELOPMENT

This invention was made with government support under grant numbers P30 EY001319 and EY028293 awarded by National Institutes of Health. The government has certain rights in the invention. The government has certain rights in the invention.

FIELD OF THE APPLICATION

The application relates to in vivo imaging and particularly to imaging, counting, and typing in vivo objects of about a cellular scale and smaller in the eye.

BACKGROUND

The retina is the light sensitive tissue at the back of the eye where the sensation of vision begins. In the vertebrate retina, light must travel through the entirety of retinal neurons before being detected by the photoreceptors. Most of the inner retinal neurons are translucent, providing a benefit for vision but also a formidable challenge to image these cells employing non-invasive microscopic retinal imaging techniques. This lack of cellular contrast in ophthalmic imaging has thus limited basic science and clinical investigation.

SUMMARY

A method to image an in vivo object in an eye includes illuminating an object in the eye by a light source; configuring one or more detectors to receive light from a conjugate plane behind a confocal plane of the object, the conjugate plane acting as a light screen; receiving at the one or more detectors a backscattered light from the light source which has been refracted at least in part by the object before being backscattered from the light screen to provide a detector data; and processing the detector data over a time period by a computer to generate information about the object.

The step of processing can include processing the detector data over the time period by the computer to generate the information about the object as a two-dimensional image. The step of processing can include processing the detector data over the time period by the computer to generate a type information about the object. The step of processing can include processing the detector data over the time period by the computer to generate the information about an internal portion of the object.

The step of illuminating the object can include illuminating a cell, and the step of processing can include processing the detector data over the time period by the computer to generate the information about a nucleus, nucleolus, or a heterochromatin of the cell. The step of illuminating the object can include illuminating at least one red blood cell or at least one white blood cell. The step of illuminating the object can include illuminating the object in an absence of a contrast agent or a label.

The step of processing can further include counting a number of red blood cells cell or a number of white blood cells in an imaged area. The step of processing includes processing the detector data over the time period by the computer to generate the information about the object to diagnose a pathology or disease of an animal or human unrelated to the eye. The step of processing can include processing the detector data over the time period by the computer to generate information about immune cell activity of an animal or human as viewed through the eye of the animal or the human. The step of processing can include processing the detector data over the time period by the computer to generate the information in a 2D image which shows at least one of a white blood cell and a red blood cell.

The step of processing can include processing the detector data over the time period by the computer to generate the information in a 2D image which shows at least one of: leukocyte (white blood cell) rolling; leukocyte arrest; leukocyte trans-endothelial migration (extravasation); microglial cell motility; and leukocyte motility in a retinal tissue of an animal or human eye. The step of processing can include processing the detector data over the time period by the computer to generate the information in a 2D image which shows a leukocyte re-entry into a vessel following resolution of inflammation.

The step of processing can include a object identification based on a ratiometric comparison of a forward scatter (FSC) detected light relative to a side scatter (SSC) detected light.

The step of processing can include a selective gating.

The step of configuring, can include configuring the one or more detectors to receive light from a surface of a layer of the eye acting as the light screen. The step of configuring, can include configuring the one or more detectors to receive light from an internal portion of a layer of the eye acting as the light screen. The step of configuring, can include configuring the one or more detectors for a split detection configuration.

The step of processing can include processing said detector data over a time period by a computer to generate images showing an immune cell migrating outside of a vessel of the eye, or an immune cell which is re-entering a vessel after fighting a local inflammation outside of the vessel.

The method hereinabove, performed in the absence of a contrast agent.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 1 illustrates a system diagram of an AOSLO that may be employed in various disclosed embodiments.

FIGS. 2A-2C illustrate various image detection techniques for the AOSLO of FIG. 1 that may be employed in various disclosed embodiments.

FIGS. 3A-3C and 4A-4C illustrate schematics of described optical model emphasizing the role of cellular refractive index, and ganglion cell images demonstrating observed asymmetric contrast.

DETAILED DESCRIPTION

Figure 3A:
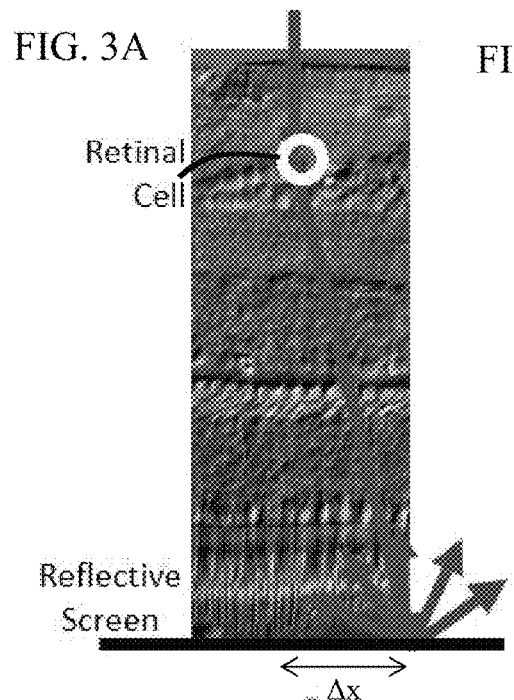
Figure 3C:
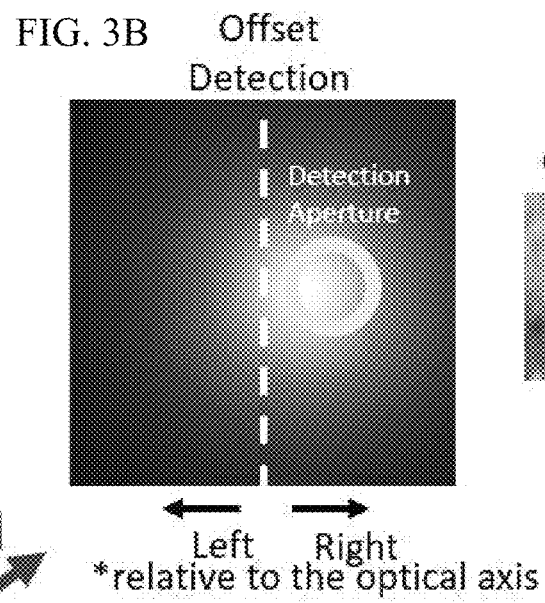
Figure 3C:
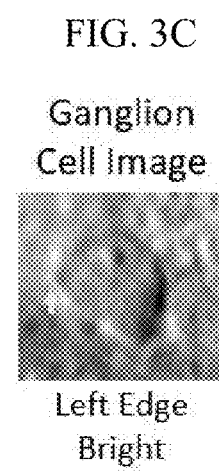

In the description, other than the bolded paragraph numbers, non-bolded square brackets ("[ ]") refer to the citations listed hereinbelow. References for each part of the Applications follow each part. The Applications is in 5 parts.

Part 1 is the parent application, U.S. patent application Ser. No. 16/205,925, LABEL-FREE CONTRAST ENHANCEMENT FOR TRANSLUCENT CELL IMAGING BY PURPOSEFULLY DISPLACING THE DETECTOR. Part 2 describes blood cell identification using comparisons of scatter in single and double pass light in the living retina. Part 3 describes optimizing translucent cell contrast in adaptive optics ophthalmoscopy. Part 4 describes how adaptive optics permits label-free intravital imaging of dynamic immune responses in the retina. Part 5 describes exemplary applications of immune cell imaging using the new method and configurations of the application.

Part 1—Label-Free Contrast Enhancement for Translucent Cell Imaging by Purposefully Displacing the Detector Recently, innovations in ophthalmoscopy have sought to optimize resolution and contrast to improve inner retinal cell imaging. To improve resolution, adaptive optics measures and corrects for aberrations of the eye. To improve contrast, non-confocal (off-axis) detection methods have been demonstrated to enhance the phase contrast from translucent retinal cells. Elsner et al. (A. E. Elsner et al., "Infrared imaging of sub-retinal structures in the human ocular fundus," Vision Research 36, 191-205 (1996), e.g., demonstrated that retinal contrast could be improved for some structures when collecting light outside the confocal region in a scanning laser ophthalmoscope by displacing the imaging aperture laterally in the focal plane from the focused illuminated spot ("offset-aperture"). Chui and colleagues (T. Y. P. Chui et al., "The use of forward scatter to improve retinal vascular imaging with an adaptive optics scanning laser ophthalmoscope," Biomed. Opt. Express 3, 2537-2549 (2012)) further applied this principle to the adaptive optics scanning light ophthalmoscope (AOSLO). Sulai and colleagues (Y. N. Sulai et al., "Visualization of retinal vascular structure and perfusion with a nonconfocal adaptive optics scanning light ophthalmoscope," J. Opt. Soc. Am. A 31, 569-579 (2014)) further modified the approach by blocking the confocal light and capturing all of the non-confocal light in two detectors. In this configuration, light to the left of the optical axis in a scanning instrument was collected by one photomultiplier tube (PMT) and light to the right was collected by a second PMT. Sulai found that normalized subtraction of the two images could further remove common information and enhance the asymmetries in the image. Sulai called his method "split-detection" and enabled resolving photoreceptor inner segments (D. H. Scoles et al., "In Vivo Imaging of Human Cone Photoreceptor Inner Segments," IOVS IOVS-14-14542 (2014)).

Using such non-confocal or off-axis detection methods, several groups have demonstrated that a variety of once essentially non-imageable cells can now be visualized in the living retina. Photoreceptor cell bodies and horizontal cells above the monolayer of photoreceptor outer segments, e.g., have been revealed employing offset imaging techniques (A. Guevara-Torres et al., "Imaging translucent cell bodies in the living mouse retina without contrast agents," Biomed. Opt. Express 6, 2106-2119 (2015)). This provided some of the first label-free images of the axial stacking of photoreceptor somas in the living retina. With further optimization, the new capabilities extended to image retinal ganglion cells (E. A. Rossi et al., "Imaging individual neurons in the retinal ganglion cell layer of the living eye," PNAS 114, 586-591 (2017)), which are responsible for transmitting visual information from the eye to the brain.

In addition to neurons, label-free imaging of the retinal vasculature and single blood cells flowing within have been shown (A. Guevara-Torres et al., "Label free measurement of retinal blood cell flux, velocity, hematocrit and capillary width in the living mouse eye," Biomed. Opt. Express, BOE 7, 4228-4249 (2016)). Coupled with fast camera acquisition, the passage of individual red blood cells in capillaries enables new measurements of blood cell flux, hematocrit, velocity in addition to capillary width. This provides new information on the delivery of metabolites in the healthy and diseased retina.

While some inner retinal cells have been successfully imaged employing offset imaging techniques, the source of the contrast has not been completely understood. It would be desirable to provide further understanding of these imaging modalities and provide a method to further optimize contrast for improved non-invasive imaging of such retinal cells.

With non-confocal, off-axis detection imaging methods such as offset aperture and split detector techniques, several studies have demonstrated new classes of cells that can be identified using safe-levels of near infrared light. Among the new capabilities provided by these studies are imaging blood vessel wall, individual red blood cells, photoreceptor inner segments, photoreceptor somas, horizontal cells and ganglion cells. Previous models of light scatter provide a partial description of contrast mechanisms. In work by Elsner et al. and further refined by Chui and colleagues referenced above, authors provide a schematic of how light is scattered in offset aperture detection suggesting that light is forward scattered and then reflected by a deeper screen in what they call multiply scattered light. While this model provides an understanding that light interactions in the retina are complex, there is no developed optical model that describes the nature of the asymmetry in the contrast characteristic of offset aperture and split-detection images, complicating further improvements of the techniques.

The present disclosure discloses an optical model of the retina that describes light interaction with the boundaries of these cells, emphasizing the role of refractive index change within the focal plane of illumination. In a simplified model, single cells illuminated by an AOSLO beam act as microscopic spherical lenses which steer the beam to the left or right depending on the polarity of the refractive index change. This not only provides a working model of the asymmetry observed in offset aperture and split-detection images, but it also enables improving the contrast and signal to noise ratio of the collected images by further improving the detector configuration to increase the contrast.

An improved approach to visualize transparent cells that does not require fluorescence and only uses light reflected by the retina is accordingly described. Wavelengths in the visible light spectrum and/or the near infrared spectrum may be employed, as is conventional in optical imaging. The approach emphasizes the role of cellular refractive index change within the plane of illumination to provide an explanation for the origin of the asymmetric contrast in offset aperture and split-detection images, and methods for further optimizing the contrast based on such model are described. More particularly, while it is known that the detector should be placed axially in the same plane as the illumination in confocal systems, the present disclosure describes methods wherein the detector is purposefully "misaligned" in a particular axial direction to provide an enhancement in the contrast and signal to noise ratio in a non-confocal, off-axis detection imaging method.

To demonstrate applicability of the described optical model in providing an improved method for imaging retinal cells, an AOSLO especially designed to image the living mouse retina as described in Y. Geng et. al., "Adaptive optics retinal imaging in the living mouse eye," Biomed. Opt. Express 3, 715-734 (2012), such as illustrated in FIG. 1, may be employed. In brief, the aberrations of the eye are measured in such apparatus using a Shack-Hartmann wavefront sensor (WFS) using 904 nm light as a wavefront sensing beacon (WFSB). The system corrects the aberrations of the eye using a membrane based deformable mirror (DM). The AOSLO is composed of five afocal telescopes that relay the entrance pupil into horizontal (HS) and vertical (VS) scanners, the deformable mirror DM and finally the pupil of the eye. These ophthalmoscopes are scanning instruments, meaning that only one spot is illuminated at a time. The imaging spot is generated with a 796 nm superluminescent diode and it moves in a raster scan pattern using a horizontal fast scanner at 15 kHz and a vertical scanner at 25 Hz. This spot is reimaged into the detector section of the ophthalmoscope, and this light distribution is called the point spread function (PSF) (FIG. 1).

A variety of confocal and non-confocal, off-axis methods have been developed by selecting different subsets of the PSF, such as confocal detection, offset aperture, and split-detection (FIGS. 2A-2C, respectively). For many years, confocal mode has been achieved by placing a circular detection aperture (DA) at the center of the PSF as illustrated in FIG. 2A, maximizing the collection efficiency while enhancing axial sectioning by rejecting out of focus light. It is known that in such confocal systems, the detector should be placed axially in the same plane as the illumination. The offset aperture method is performed by displacing the aperture laterally from the center of the PSF as illustrated in FIG. 2B, and split-detection is performed by separately detecting the left and right portions of the PSF as illustrated in FIG. 2C (e.g., employing photo multiplier tubes PMT1 and PMT2) and then calculating the normalized difference between the two channels.

Although these benefits can be easily transferred to human imaging, the mouse eye may be chosen to advantageously demonstrate the described optical model because it has a large numerical aperture of 0.49 providing optical sectioning in the plane of illumination. The axial resolution improves as the square of the numerical aperture and in the mouse, the numerical aperture is twice as large as that of the human, making the depth of focus four times better in the mouse eye and improving the capabilities to distinguish layers of individual cells. To mitigate the biological variability, every experiment should be repeated in a plurality of mice.

Figure 4A:
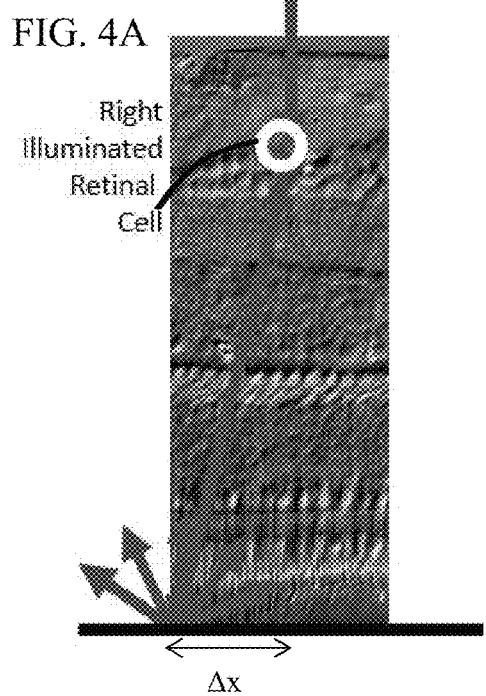
Figure 4B:
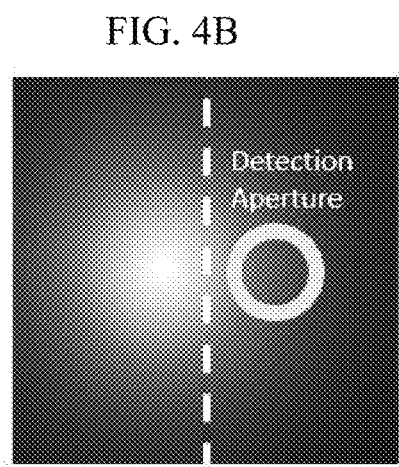
Figure 4C:
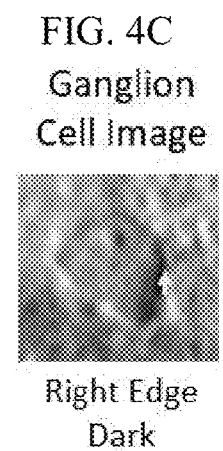

Optical Model: Forward Beam Deviations Due to Changes in Refractive Index Coupled with Deeper Backscattering Layers The present described model considers three steps of light interaction in the retina that are important for providing cell contrast and asymmetry. A simple way to understand this optical model is to consider a cell as though it were a microscopic spherical lens. The aberration corrected spot in an AOSLO is smaller than the average size of the cell found in the retina. When this spot illuminates either the right or left portions of a retinal cell (depicted as the white circle in FIGS. 3A and 4A) as schematically shown in FIGS. 3A-3C and 4A-4C, respectively, the focused beam will be deviated into opposite directions. This beam deviation will be propagated into deeper reflective layers in the retina creating a light distribution that is displaced from the optical axis by a distance $\Delta x$ as shown in FIGS. 3A and 4A. This displacement will be re-imaged into the detector plane by the AOSLO maintaining the deviation from the optical axis as shown in FIGS. 3B and 4B. With a non-confocal, off-axis detection scheme decentered relative to the optical axis like offset aperture and split-detection, light in one detector will increase when imaging one edge of the cell relative to the other providing asymmetric contrast as shown for ganglion cell images in FIGS. 3C and 4C obtained by split-detection imaging. By coupling with an offset detection aperture in the same direction as the beam deviation, e.g., this will provide a bright pixel in the left edge (FIGS. 3A-3C), while when the offset detection aperture is in the opposite direction as the beam deviation, less light will be coupled through the aperture, providing a dark pixel in the right edge (FIGS. 4A-4C).

Figure 5:
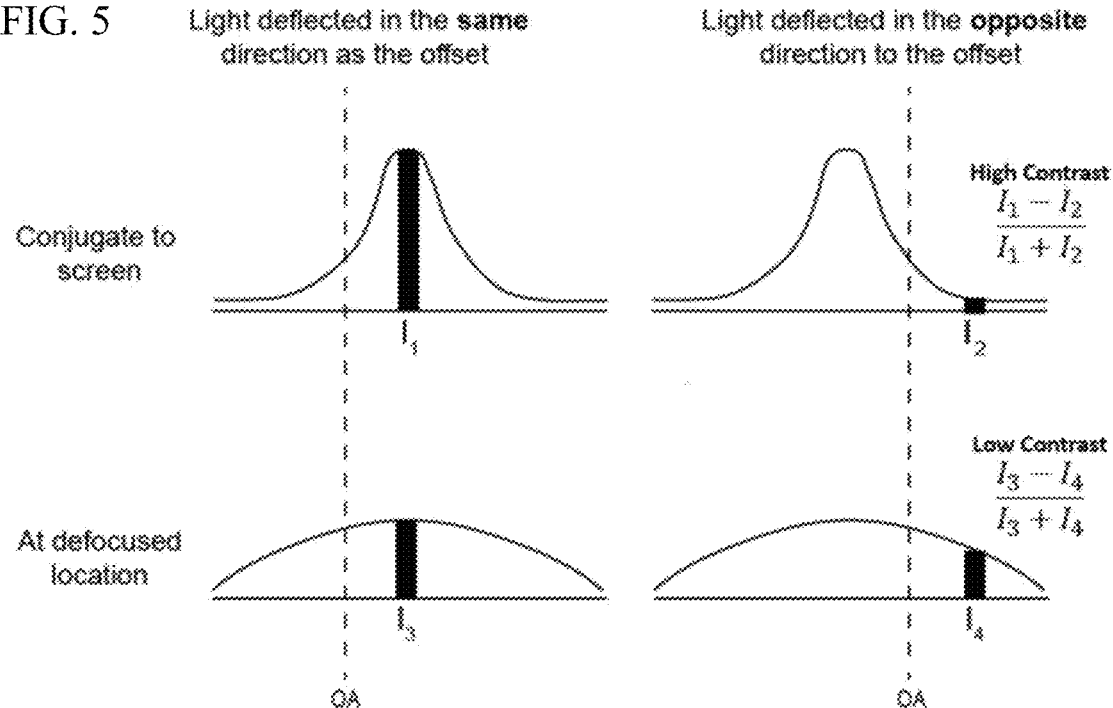
FIG. 5 illustrates a schematic diagram showing light intensities relative to distance from optical axis and the rationale for an increase in the contrast when a detector is axially located at a position conjugate to a detection screen.

This model suggests that when only one edge of the cell is illuminated as the imaging beam is scanned, light is deviated away from the optical axis (OA). As shown in FIG. 5, when this deviation is coupled with an offset detector in the same direction, this will yield a high detected intensity $I_1$ when the detector is conjugate to the screen (i.e., a bright pixel), while when light is deviated in the opposite direction, less light couples through the offset aperture, as the light distribution is highly peaked, and a low intensity $I_2$ is obtained. The difference in intensities relative to the sum will thus provide relatively high contrast in the final images. As the reflection from the screen is assumed to be diffusive, defocus will be added when the offset detector is at any other plane, broadening the decentered light distribution and the difference in intensities $I_3$ and $I_4$ will be smaller relative to the sum further diminishing the contrast. The same analysis can be applied to split-detection or other off-axis detection schemes decentered from the optical axis.

Experiments Testing Optical Model

An AOSLO as described above was used in an offset detection configuration for imaging retinal cells in the mouse eye using aperture diameters between 8 and 40 Airy Disk Diameters (ADD) and displacements between 10 and 50 ADD. The detector aperture is attached to the PMT and move in a three-dimensional stage. The first step is moving the detector axially to the position beyond photoreceptors and this may yield a local maximum in the contrast. In a second step, the plane of illumination is moved to the detector plane that maximizes contrast and this may reveal the mosaic of photoreceptors.

Figure 6:
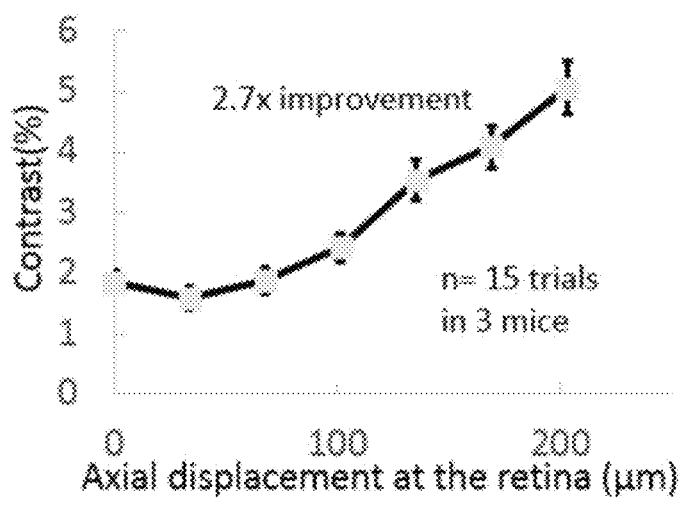
FIG. 6 illustrates data collected in the mouse eye showing a 2.7-fold increase in the contrast when the detector is displaced axially towards the photoreceptors.
Figure 6:
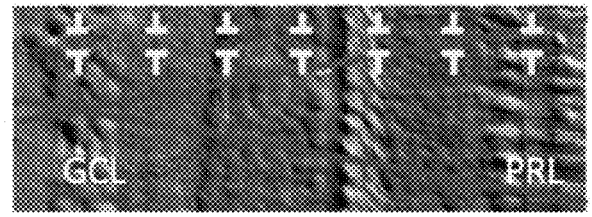

The obtained data as shown in FIG. 6 shows an enhancement in the contrast when the detector is axially displaced from a plane conjugate to the imaged cell layer (ganglion cell layer GCL) a distance beyond a depth of field of the light source focused at the imaged cell layer towards a plane conjugate to a deeper reflective screen (photoreceptor layer PRL). In these experiments, vessels in the ganglion cell layer (GCL) were imaged, and an axial displacement of the detector reached a location close to conjugate to the photoreceptors (PRL). A 60% increase in the collected efficiency and a 2.7-fold increase in the contrast was observed when performing the axial displacement in the detector while imaging these vessels. This example demonstrates that by displacing the detector axially to a position conjugate to a layer of known strong retinal reflection, like the photoreceptor layer, the image contrast will increase.

Strong reflections may be observed from multiple retinal layers. Despite this, a local maximum in the image contrast is expected when the axial displacement is close to the strong reflection of the photoreceptors, or to a plane conjugate to the interface between the choroid and the sclera. In this model, the retinal reflections are assumed to be diffusive. Van Blokland and Van Norren (G. J. Van Blokland et al., "Intensity and polarization of light scattered at small angles from the human fovea," Vision Research 26, 485-494 (1986)) observed two components of the retinal reflection, a wide angle scattered component and a directional one. Even if the two components are present, an improvement from the wide-angle scatter component is still expected to be obtained, and in fact the data shows such an improvement in the contrast and collection efficiency with an axial displacement towards the photoreceptors. The diffuse assumption is also consistent with the double pass-incoherent image based methods to measure ocular aberrations (P. Artal et al., "Odd aberrations and double-pass measurements of retinal image quality," Journal of the Optical Society of America A 12, 195 (1995); J. Santamaria et al., "Determination of the point-spread function of human eyes using a hybrid optical-digital method," Journal of the Optical Society of America A 4, 1109 (1987)).

General Summary and Introduction to Parts 2 and Beyond

Generally, imaging of the structures of the eye has used detectors focused directly in the plane of the object to be observed (detectors configured to be confocal with the object). Light from planes other than confocal with the object or surface being imaged has been intentionally rejected and thus not registered by the detector. Even over the last twenty years or so where SLO and later AOSLO have been developed, the detectors of the AOSLO have been configured so as to be confocal with the object to be imaged by laser scanning. The adaptive optics advance of the SLO made it possible to compensate for optical imperfections of the cornea and lens which immensely improved images taken at and near the retina of the eye. However, still the common wisdom has been to set the AOSLO detectors confocal to the object or surface of interest.

For those less experienced with AOSLO apparatus, a note on generating the 2D exemplary images of the Application follows at the end of this general summary.

As introduced in part 1, and now further developed in parts 2 and later, we realized that by configuring the AOSLO detectors behind the object of interest, i.e. confocal with a plane behind the object of interest, provides an increase in contrast without a need for contrast agents. Since the work of part 1, we realized that we can now literally image the internal portions of the objects, such as cells, including views of the cell nucleus, nucleolus, and heterochromatin. Moreover, also since the work of part 1, we can now literally type the cells, including typing of individual cells.

To better understand the surprising results of our new imaging methods based on backscatter from a plane behind the object to be observed, note that the physical distances are typically at the cellular level. For example, when imaging a cell at the back of the eye, as described hereinabove, the common wisdom has been to place the imaging detector, e.g. an AOSLO detector, confocal with the cell. Detector configuration forward or rearward of the object has been considered to be an imaging configuration error. Moreover, conventional AOSLO apparatus specifically reject light from behind the confocal plane of the object or surface being imaged (e.g. by pinhole and detector placement).

Now, according to the new method of the Application, we intentionally configure the detector (at least one detector) to be confocal with a plane behind the object to be imaged. For example, an AOSLO laser spot might be on the order of 9 μm axially with an effective depth of focus of just a few μm. According to the new method, the detector might be moved about 14 mm from a traditional detector configuration, for a change in the conjugate plane to a plane now 130 μm behind the cell. We sometimes refer the new plane as a "screen" behind the object. While 130 μm is less than the thickness of a human hair, in the context of imaging objects at the back of the eye, 130 μm is a relatively large distance, well outside of what light would have been imaged by one or more detectors during the scanning of the laser beam of the AOSLO. Now, the backscattered light that is received by the detector configured to be conjugate to the screen behind the object, includes light that has been refracted by the object, here by the cell, then reflected as backscatter light off the screen.

Note that while the new method can be achieved with only one detector, typically two or more detectors are used. The two or more detectors can be configured to detect a variety of different parameters, such as wavelength, polarization, etc., as well as while at the new configuration confocal with a plane behind the object, typically looking from different angles. Moreover, one or more of the detectors can add a view of a plane confocal with the object, however, such additional information is not needed. the emphasis of the Application, the backscattered light detected from a plane behind the object, a screen behind the object.

The images shown throughout the Application are generated from one or more detectors using typical AOSLO imaging apparatus with the new configurations of one or more detectors and new methods of the Application. For those less familiar with AOSLO instruments, the scanning of the AOSLO laser beam is what provides the two-dimensional aspect of the images derived from one detector, or combinations of information from two or more detectors. The known routines which map the detector signal information (e.g. an analog signal digitized from a typically AOSLO photomultiplier tube (PMT) detector correlate the detector data to the known corresponding position or direction of the laser beam at any giving moment of time to the detector data at that moment.

Detectors data is typically processed in time by a computer associated with the imaging apparatus, typically an AOSLO. Typically, detector data, such as PMT data is an analog signal which is digitized an input to a computer. The computer associates the digitized data in time with a known position of the illumination, typically a laser beam, to generate a 2D image and/or to process object data for given position in the area being imaged or scanned. While the examples generally related to building an image and/or analyzing object size data and/or counting objects and/or imaging the contents of the object, based on a laser beam correlated to detector data in time, any other suitable illumination and detection (e.g. area imaging by a 2D sensor) can be used for the new method which images a conjugate plane behind the object. See also the section on AOSLO 2D image generation at the end of this section.

Also, generally the new methods of the application are useful for viewing translucent objects. The new methods exploit light refracted by at least part of the object (the laser spot is typically, but not necessarily, smaller than the object being observed). Because of changes in the refractive index of parts of the object, the backscattered light when received from the screen of the plane behind the object and mapped in to an AOSLO image contains the new information with increased contrast that may come from beam deviations by the cell of interest, and now since the work of part 1, with an ability to image and type objects such as cells as well as component parts of the cells. We refer generally to the translucent nature of the objects being imaged, however the new method can also be used with transparent structures or objects, so long as there is a change in the refractive index as the AOSLO laser passes through the object, or a portion of the object.

Also, while we refer for simplicity to the plane behind the object as a screen, in more detail, such screens often have irregularities, and typically may not be perfectly flat over the AOSLO scanned area of the image. Knowledge of particular types of structures used as the screens can be used to further correct images derived from the backscattered light from any particular type of screen (i.e. the plane behind the object chosen to be conjugate with the one or more detectors).

Screens can have varying thicknesses. Where the reflective screen is relatively thick (e.g. in a range of about 5 to 100 μm, the detector can be displaced to a conjugate position inside the thick layer, which in some cases can provide detector data more optimal for imaging, typing, and/or counting objects.

AOSLO images derived from light refracted by a translucent object and viewed by the detector from a screen behind the object may or may not "look" exactly like the object being imaged. Some details of such images indicative of structure shapes, sizes, or type, may or may not be literal representations of an actual optical view taken in a plane conjugate with the object. However, in all cases, the contrast is substantially improved over the normal "glints" seen in confocal imaging.

Because of the enhanced contrast of objects imaged by the new method, imaging comparable to or better than imaging with labeling or contrast agents can be achieved. Other than when used for alternate method verification or proof of principle studies, the new method and configuration of the Application allows for "label-free" imaging and does not use or need supplementary contrast agents or labeling techniques or agents.

While the examples of the Application are AOSLO based, any type of 1D or 2D imager using a detector or a sensor which can be configured to be conjugate to a plane behind an object to be imaged (as opposed to confocal with the object) can perform the new method of the Application. Laser scanning instruments are particularly well suited because the spot illumination size is typically on the order of, or smaller than the objects being observed. However, the broader concept of imaging (detecting) backscatter light from behind an object, which has been refracted by at least part of an object is believed to be generally useful beyond only laser scanning imaging apparatus.

With this new ability to image, type, and/or count objects in the eye, an entirely new range of animal and human analysis is made possible. For example, there can now be the equivalent of many types of blood panels which previously required that blood be drawn and sent to a laboratory for further analysis. However, because animal and human blood generally flows through the body, blood cells can now be typed and counted by the method of the Application by viewing cells, such as, white blood cells and red blood cells by directly viewing the blood cells in near real-time in vivo directly through the eye. A blood draw is no longer necessary. Similarly, immunology and complete blood count (CBC) analysis can be performed through eye, such as by counting white blood cells, or determining the ratio of the number of white blood cells to the number of red blood cells.

Note on 2D AOSLO Image Generation

The examples of the Application are based on data generated by one or more detectors of an adaptive optics scanning laser ophthalmoscope (AOSLO) apparatus.

The generation of the 2D images in an AOLSO using a raster scan has been described extensively in previous publications (e.g. A. Guevara-Torres et al., "Imaging translucent cell bodies in the living mouse retina without contrast agents," Biomed. Opt. Express 6, 2106-2119 (2015)). The first step in image generation is to capture a single pixel. To do this, a point source like an optical fiber sends light into the AOLSO. The settings of the AOSLO can be adjusted so that the light is focused at the retinal plane where the cell of interest is located. Light is reflected or backscattered from structures at the layer of interest or now, as per the new method of the Application, from retinal structures behind or deeper than the object being observed. As described herein, those structures can act as backscattering screens. Then light that leaves the eye is recoupled into the AOSLO and can be detected, for example, as described in parts 1 and 3 of the Application with one or multiple detectors. The process described above collects a single pixel of the image and can be performed, for example, at a rate, for example, of about 40 MHz The next part of the process is to collect a line of pixels by moving the illumination spot at the retina with the fast scanner at a rate that can be, for example, about 15.5 kHz. Now that the AOSLO captured a line, and the next step is to collect a 2D frame by also moving the slow scanner in the orthogonal dimension to capture multiple lines sequentially generating a complete 2D frame. The frame rate can be, for example, about 25 Hz, and a higher signal to noise ratio can be achieved by averaging multiple 2D frames.

Techniques of AOSLO line scan imaging were also described in detail in U.S. patent application Ser. No. 61/933,102, SYSTEM AND METHOD FOR OBSERVING AN OBJECT IN A BLOOD VESSEL, and also assigned to the University of Rochester. The '102 application is incorporated herein by reference in its entirety for all purposes.

Part 2—Blood Cell Identification Using Comparisons of Scatter in Single and Double Pass Light in the Living Retina A traditional flow cytometer provides enhanced images ex vivo by processing various filtered light with N detectors. The light illuminates cells from one side and images transmitted light on the other side of the cells. Such imaging techniques are not possible in the prior art for in vivo structures (e.g. for imaging cells and other objects in the eye), because while illumination can be accomplished, such as through the front of a human eye, there is no way to place a detector directly "behind" the cells at the back of the eye.

We solved this obstacle by considering the eye as a double pass light system; that is a light from a source traveling into the eye, interacts with the cells in the back of the eye as it transilluminates and travels through them, then is back scattered by a deeper reflective layer at which time the light travels back out of the eye. We use this double-pass nature of light to determine blood cell type based on the light interaction with the single blood cells. An aspect of this invention describes an optimal configuration to place a forward and side scatter detection aperture(s) in a plane conjugate to a deeper reflective screen. Measurement and comparison between 1 and N detectors that measure forward and side scatter indicate proportional amounts of forward scatter relative to side scatter (in addition to spectra, absorption, reflection and refraction among other light interactions). Such ratio of scatter types serves to indicate the cell type that has been evaluated. The methods and apparatus are now described in more detail hereinbelow.

The new method uses the living eye as an optical system through which individual blood cells may be identified, characterized, classified and evaluated within the living body. The new method has the potential to evaluate disease and therapy non-invasively and in real-time. The new method uses a comparison of different types of light scatter to identify blood cell type.

Figure 7:
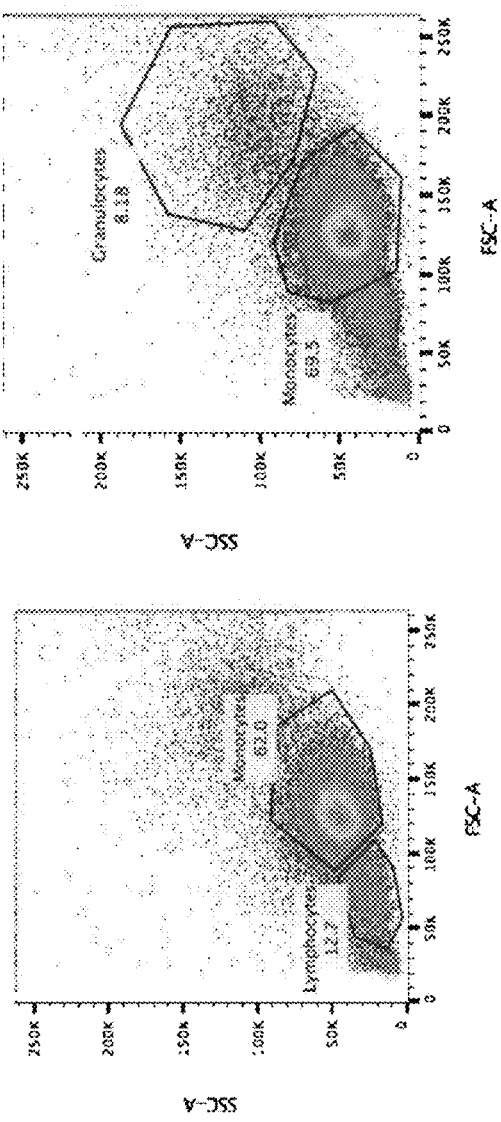
FIG. 7 is a drawing with exemplary data graphs showing an exemplary configuration of a traditional flow cytometer.
Figure 7:
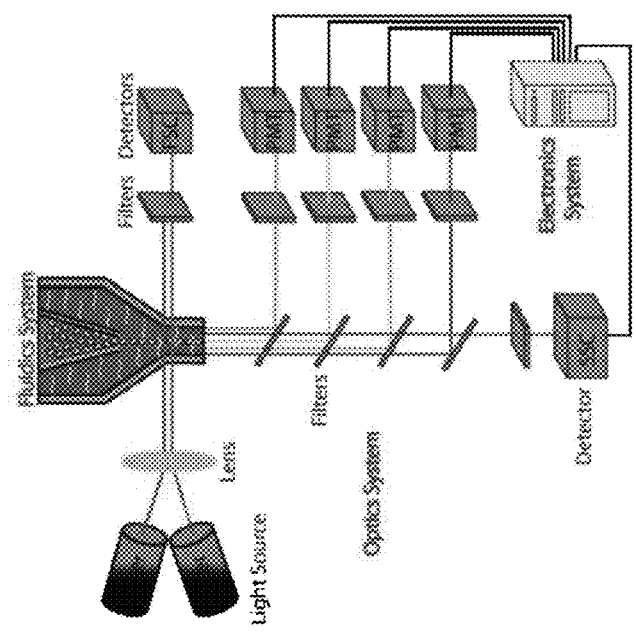

FIG. 7 (adapted from: https://www.tlowjo.com/learn/tlowjo-university/flowjo/getting-started-with-flowjo/58) is a drawing with exemplary data graphs showing an exemplary configuration of a traditional flow cytometer. Shown on the left side of FIG. 7 is a schematic of a microfluidics head with transillumination illumination/detection where the source is on one side of sample, and the detector on the opposite of the sample (e.g. blood cells). The flow cytometer measures forward scatter (FSC) relative to side scatter (SSC) which provides a ratio by which cells can be classified into different kinds of white blood cells. In such a conventional benchtop flow cytometer, the comparison of forward and side scattered light is used to evaluate whether passing blood cells in a microfluidic device indicate different subpopulations blood cells (FIG. 7). In many such devices, imaging light transilluminates the sample with a light source on one side of the sample, and a light detector on the opposite side of the sample.

Forward scattered (or non scattered) light is detected in a device along (or close to) the axis of the principal ray of the interrogation source. Side scatter is detected by a detector that is laterally offset from this axis. Such detectors measure the light that is refracted or scattered away from the unscattered (unrefracted) axis.

Figure 8:
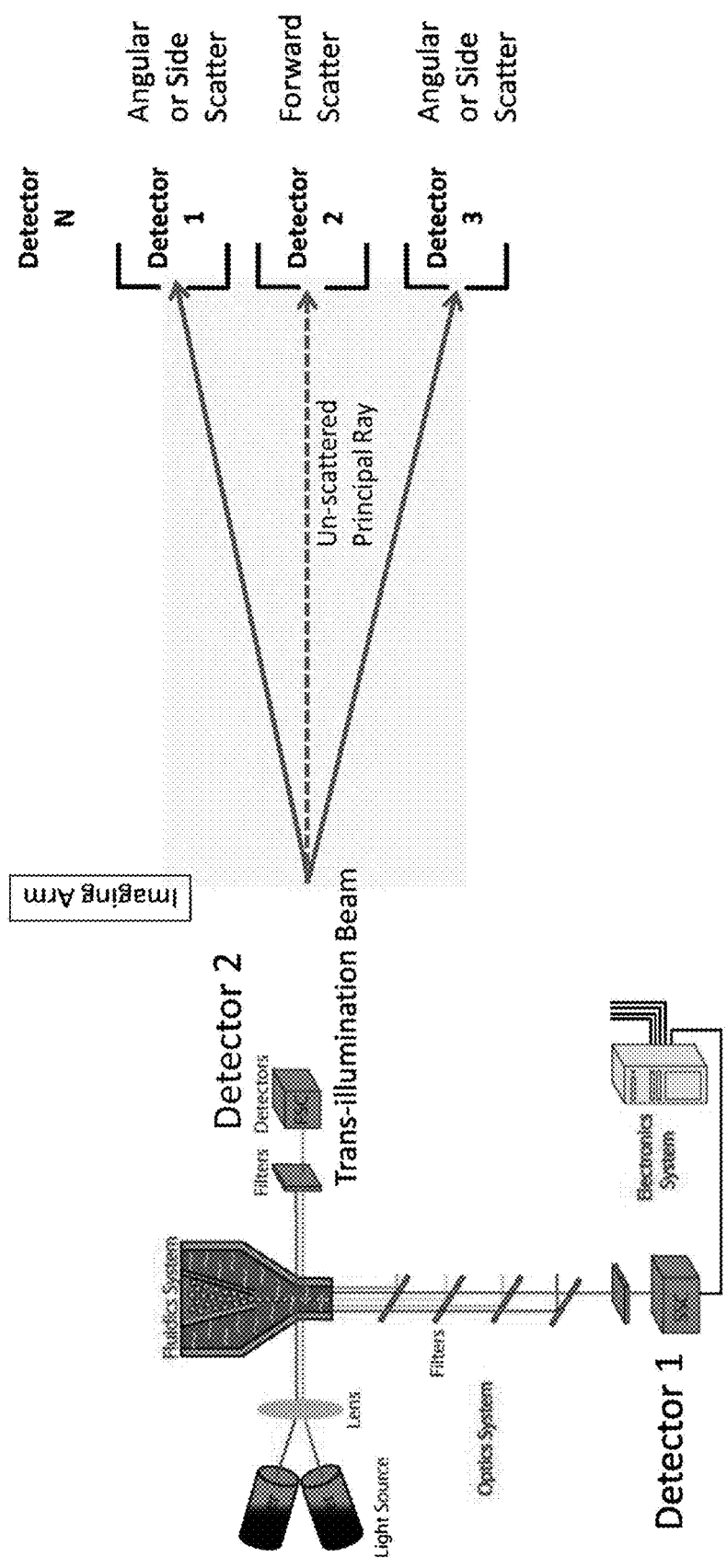
FIG. 8 is a drawing showing exemplary scatter detector configurations.

FIG. 8 (modified from: <https://www.flowjo.com/learn/flowjouniversity/flowjo/getting-started-with-flowjo/58>) is a drawing showing exemplary scatter detector configurations. The proportion of forward to side scattered light acts as a bioreporter of blood cell type at any moment of time (FIG. 8). Such an approach can evaluate the forward and side scatter using different spectra of light which not only provides measure of scatter, but also wavelength dependent scatter and absorption. Benchtop flow cytometers are ex vivo evaluation systems, where cells flow by a beam in a man-made apparatus.

It is more challenging to make such a measurement in the living body. Often, the interrogation light source and the detector cannot be positioned in a trans-illumination configuration (emitter on one side, detector on the other side). This is especially true when the objective is to measure single file blood flow (such as in capillaries where single blood cell flow is realized in the living body). To harness the utility of using cell refraction and scatter as bioreporters useful for detection of blood cell type, it is important to limit the scatter imparted from other objects in "thick" samples. The animal or human eye can serve as a low scatter window through which blood cell scatter can be measured and reported.

The new method described by the Application solves this obstacle of real time measurements of cells in an animal or human living body by considering the eye as a double pass light system.

According to the new double pass system of the Application, light from a source traveling into the eye, interacts with the cells in the back of the eye as it transilluminates and travels through them, then is back scattered by a deeper reflective layer at which time the light travels back out of the eye. The new method can use this double-pass nature of light to determine blood cell type based on the light interaction with the single blood cells.

It was realized that an optimal configuration to place forward and side scatter detection apertures are in a plane conjugate to a deeper reflective screen. Measurement and comparison between 1 and N detectors that measure forward and side scatter indicate proportional amounts of forward scatter relative to side scatter (in addition to spectra, absorption, reflection and refraction among other light interactions). Ratios of scatter types can serve to indicate the cell type that has been evaluated.

Using this approach, cell classes of individual blood cells can be non-invasively determined as cells pass by the interrogation beam in single file.

Figure 9:
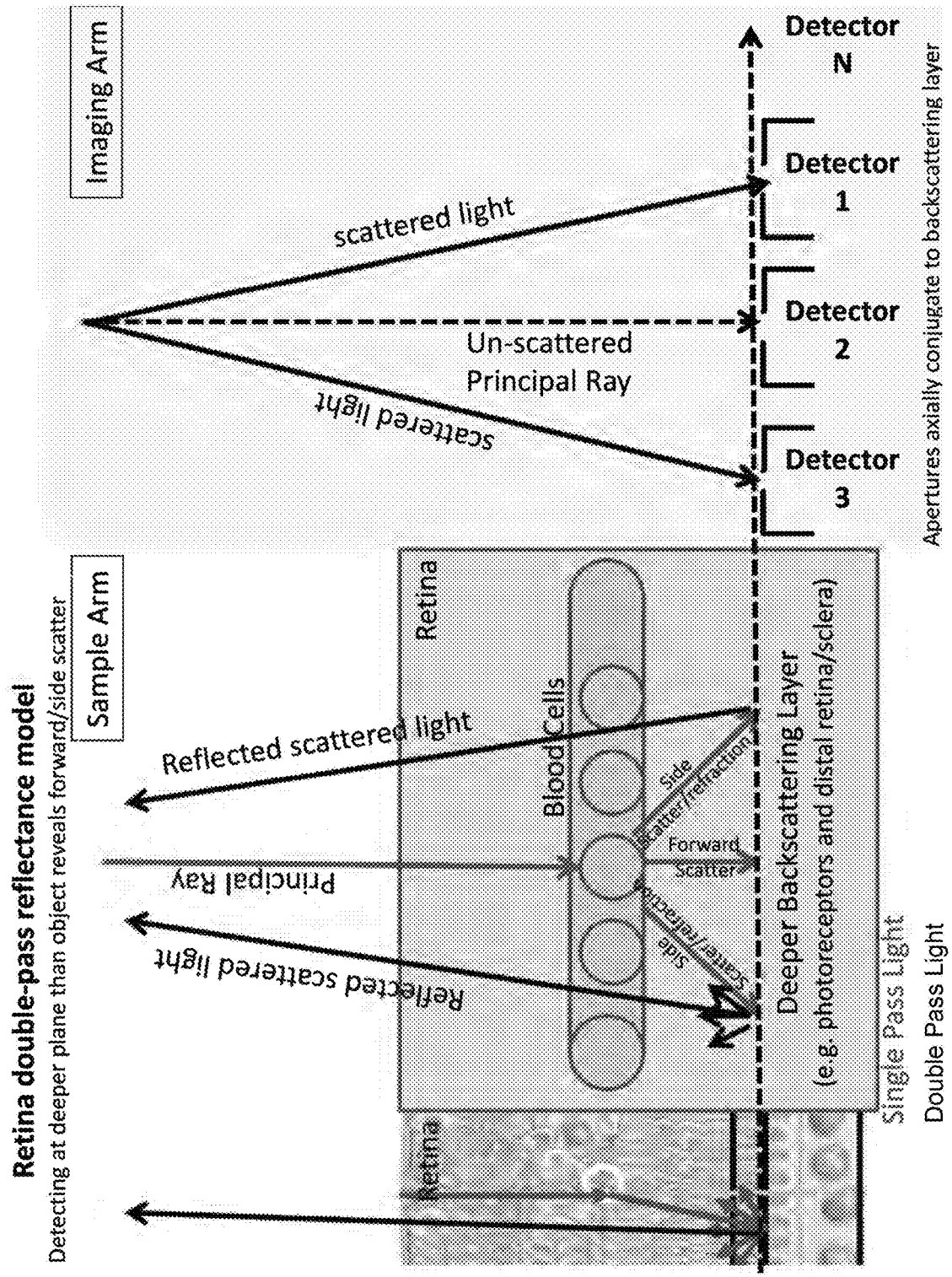
FIG. 9 is a drawing showing a retina double-pass reflectance model according to the new method and configuration of the Application.

FIG. 9 is a drawing showing a retina double-pass reflectance model according to the new method and configuration of the Application The detector apertures are placed at a deeper reflective screen with the intention of measuring the cell scatter (and refraction). Detection at a deeper plane provides more opportunity for the light to interact with the target object (FIG. 9). This new configuration holds a distinct optical advantage over the conventional strategy which images objects in a plane conjugate to the object (e.g. blood cell).

Figure 10:
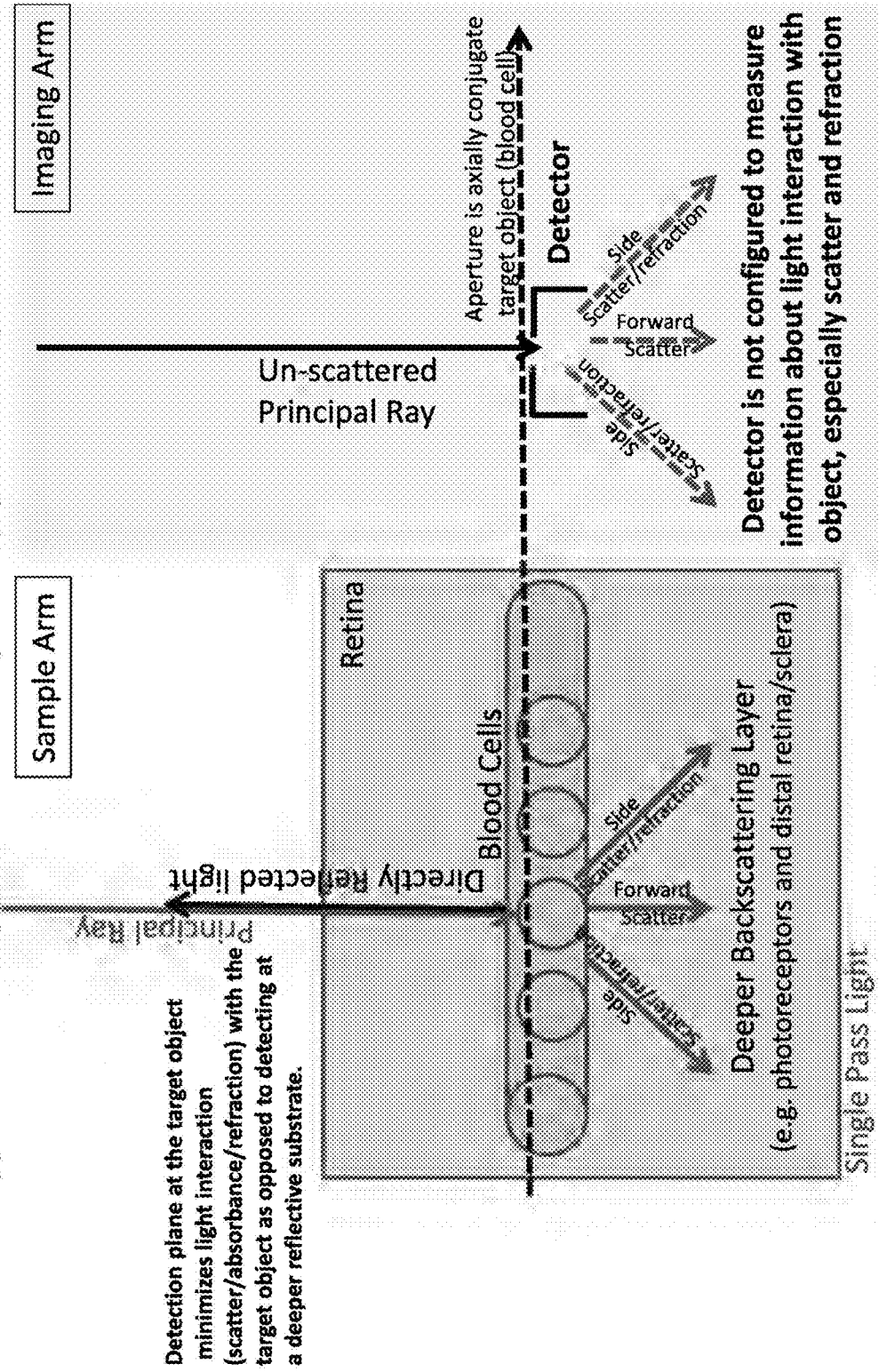
FIG. 10 is a drawing showing the suboptimal performance of where the detection aperture is conjugate to the plane of the object being observed.

FIG. 10 is a drawing showing the suboptimal performance of where the detection aperture is conjugate to the plane of the object being observed. FIG. 10 shows a conventional imaging approach whereby the interrogation object is in the same axial conjugate plane as the detector. In such a configuration, the imaged object is dominated by reflection "glints" which is a feature of the refractive index mismatch of the target object and its surround. Such glints represent a surface property of the cell and therefore contain minimal information about cell scatter, refraction or photon interaction with the entire volume of the target object.

Figure 11:
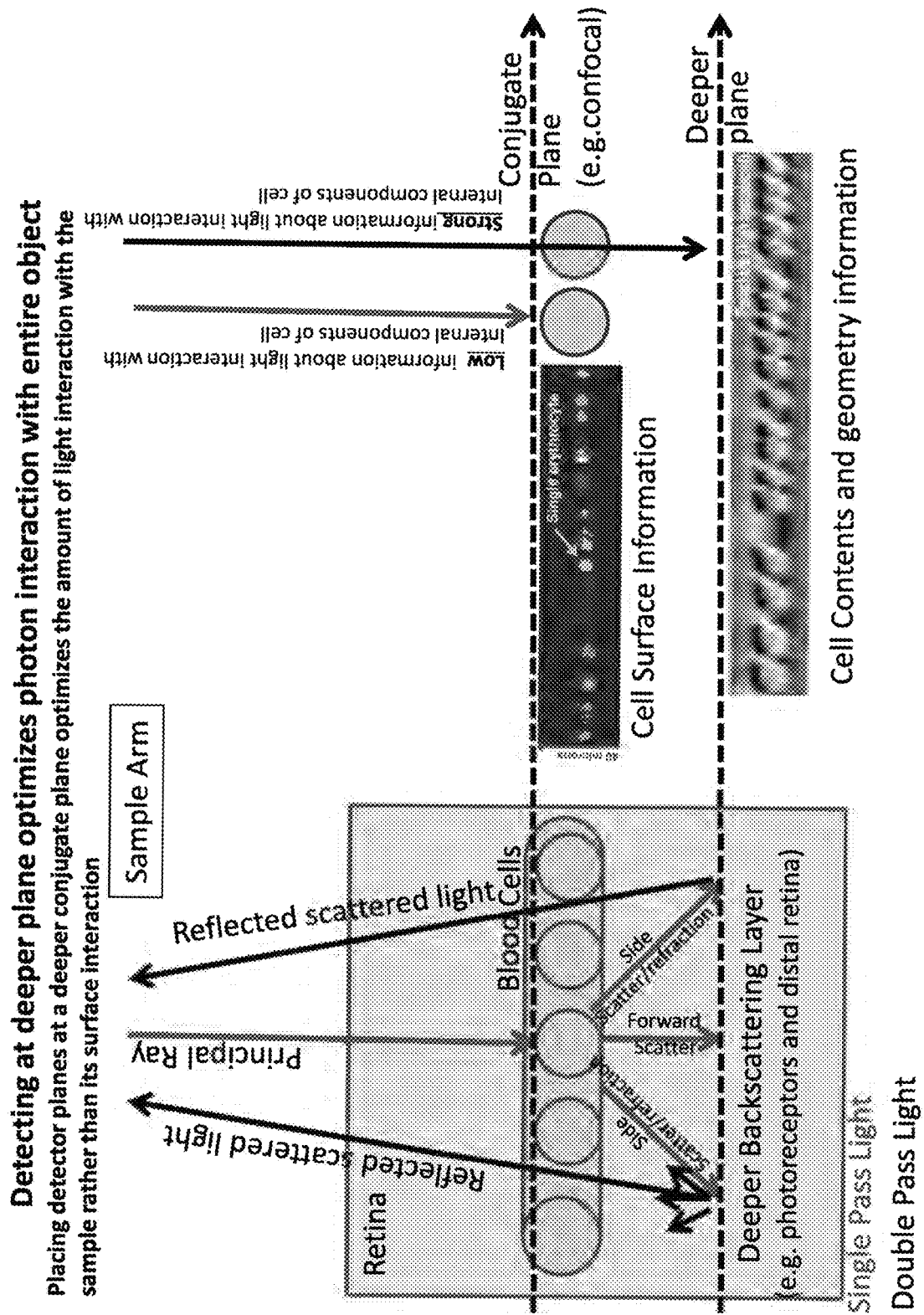
FIG. 11 is a drawing showing detection at a plane deeper than the object plane according to the Application.

The Application describes a new way to measure the forward vs side scatter components to classify cell type. The new method and configuration detect double-pass forward and side scatter is shown in FIG. 11. FIG. 11 is a drawing showing detection at a plane deeper than the object plane according to the Application. In general, the new method uses a beam of light entering the retina, and a blood vessel is imaged (e.g. FIG. 9). In the exemplary case of capillaries, blood cells flow past the beam in single file as they progress through the vascular circulation. As the light strikes the sample (e.g. single blood cell) some fraction of light is absorbed, some fraction of light is refracted, some fraction of light is minimally scattered (travels through the sample without deviation), and some of the light is strongly scattered (traveling in a path offset from the axis from which it was illuminated).

Using confocal theory, which rejects out of plane light, a series of apertures are positioned in a plane which is deeper than the target object. The new method uses this deeper plane to reflect light back to the detectors after it has traveled through the interrogation object (e.g. a blood cell).

Figure 12:
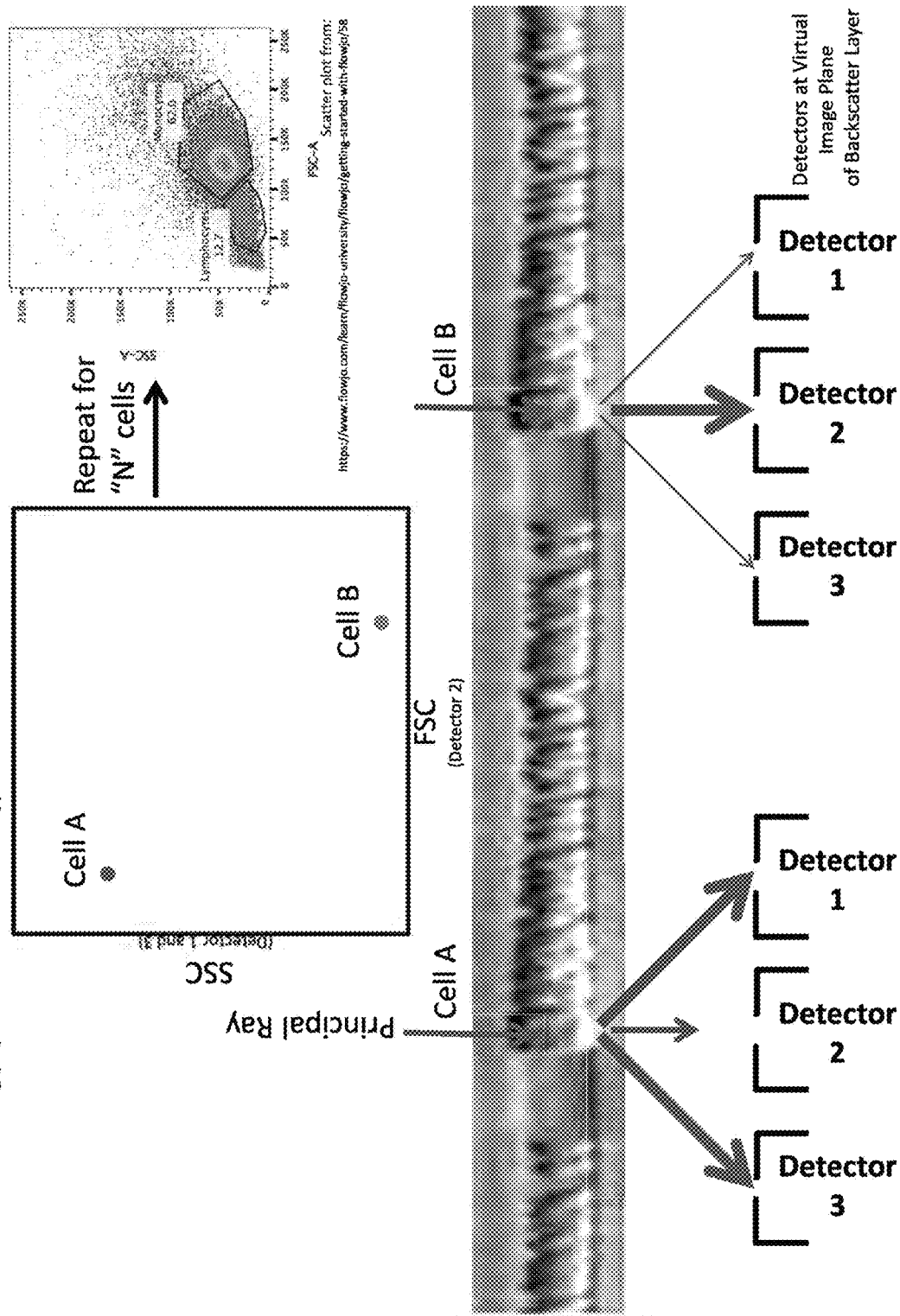
FIG. 12 is a drawing showing exemplary cells with different scatter profiles that reveal cell identity in a ratiometric plot.

In the case of the retina, when a column of blood cells in the retina is illuminated, light continues in the same general forward direction, but with vectors that are slightly deviated from the original principal ray axis of the system. These vectors represent both light refraction and types of light scatter. By placing one or more apertures at this deeper reflective plane, the proportion of forward scattered light vs side scattered light can be determined. The comparison of data from two or more detectors at this plane can reveal the amount of light scatter in the blood cell, thereby revealing its type (e.g. granulocytes, monocytes, basophils, eosinophils, red blood cells, platelets, etc.) (FIG. 12). FIG. 12 is a drawing showing exemplary cells with different scatter profiles that reveal cell identity in a ratiometric plot.

It was realized for this new method that the detectors are set to a plane conjugate to the deeper reflective screen (e.g. photoreceptors, see FIG. 9). In such configuration, the light comparison emphasizes the forward propagated light. In this way, the retina acts as a proxy to emulate transverse illumination paradigms of the prior art for ex vivo evaluation (e.g. FIG. 7).

The imaging light of the new method and configuration of the Application also allows for direct imaging of the blood cell based on its spectral refraction, absorption, and scatter by placing the detector in a deeper retinal plane (FIG. 12). Using such information, the measurement beam can be "gated" in such a way that the imaging channel reports when a cell is present. When a cell has been identified, the scatter measurement can be gated to the desired object (FIG. 13).

Figure 13:
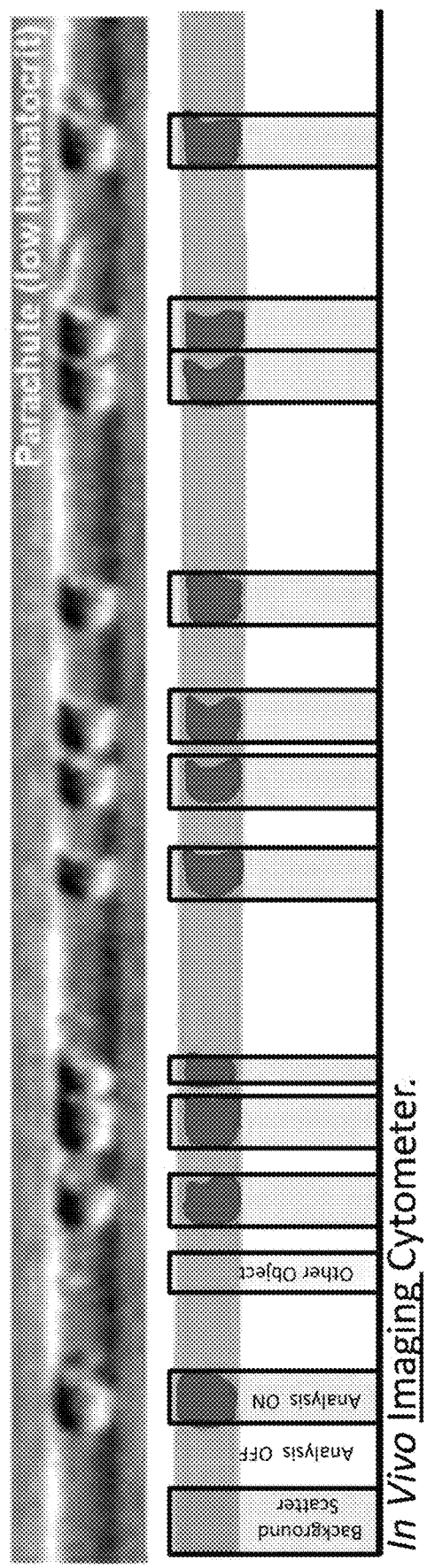
FIG. 13 is a drawing showing an exemplary imaging gate.

FIG. 13 is a drawing showing an exemplary imaging gate. Analysis "gates" allow scatter measurements to be gated in time to only when cells of a specified size/geometry pass the beam example utility: ratio of background scatter: Analysis ON by FSC or SSC of target object (akin to cuvette blanking); other object identification by removal of confounding scatter signals from off target objects; and ratio of background scatter: other object by new subpopulation analysis gated by object morphology. This selective gating can perform scatter measurements when a cell/object is present vs not present. Selective gating offers a number of advantages. First, it allows a measurement similar to "cuvette blanking" meaning background scatter can be measured when no object is present. No object measurements are important because the retina contains many such cells and removing the contribution of the background and transilluminated tissue is important for baseline measurements. Baseline measurements can remove noise and account for the other substrate that the light must pass through (such as retina, blood vessel, blood plasma etc.). Second, the gating strategy allows cells to be identified and categorized on their shape and morphology. Shape and morphology provide important information that can be combined with scatter measures to give further sensitivity and specificity to the scatter measurements. For example, forward and side scatter measurements could be performed on only on white blood cells, or only on platelets or only on red blood cells or other endogenous or exogenous bodies based on size and morphology. The spectral scatter signal would therefore be further refined to just target objects of interest increasing sensitivity and specificity of the measurement.

Figure 14:
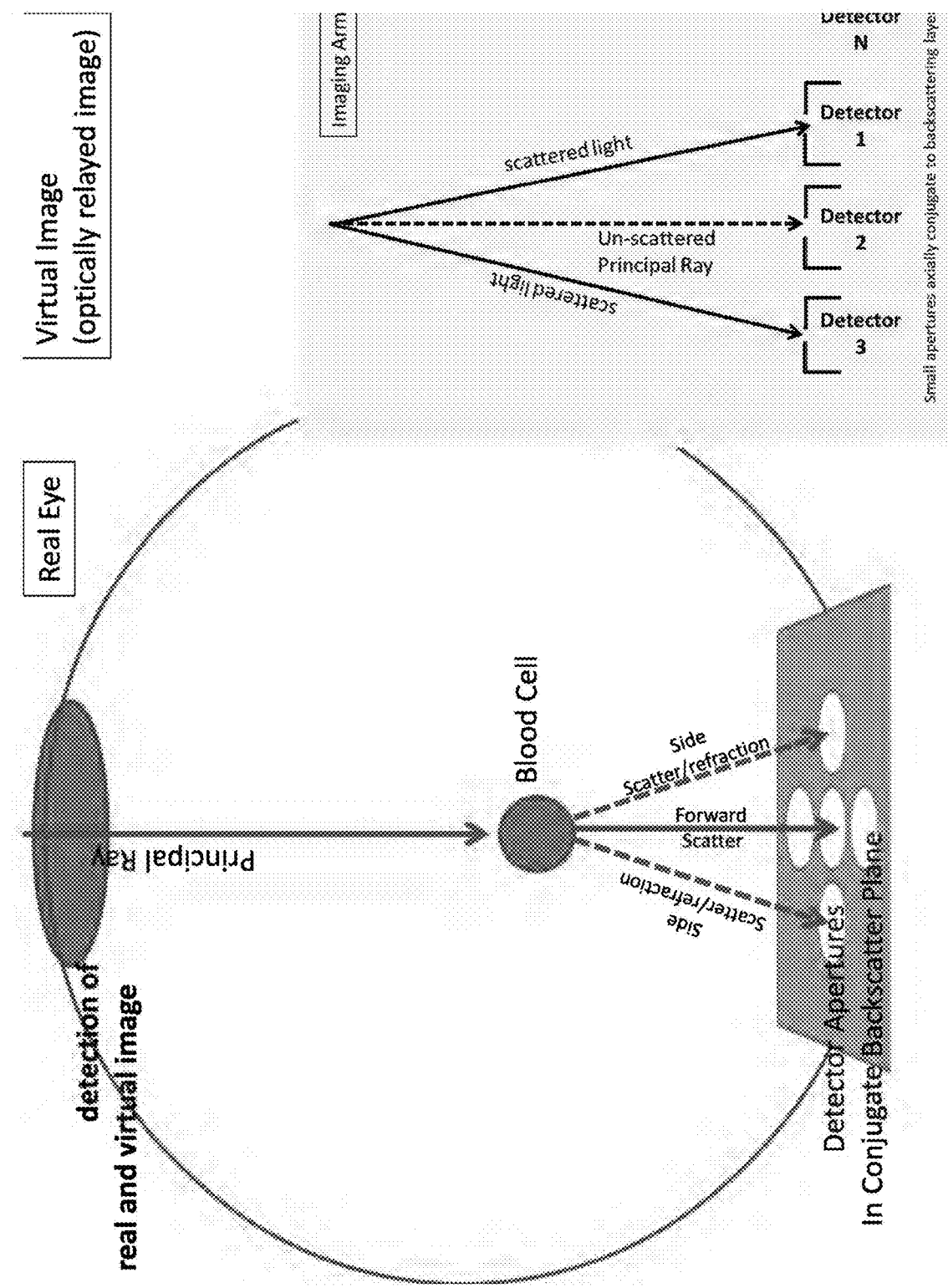
FIG. 14 is a drawing showing detection of light from a conjugate backscatter plane.

FIG. 14 is a drawing showing detection of light from a conjugate backscatter plane. FIG. 14 shows a real and virtual image of the blood cells imaged and an example detector configuration that can differentially measure forward and side scattered light.

Figure 15:
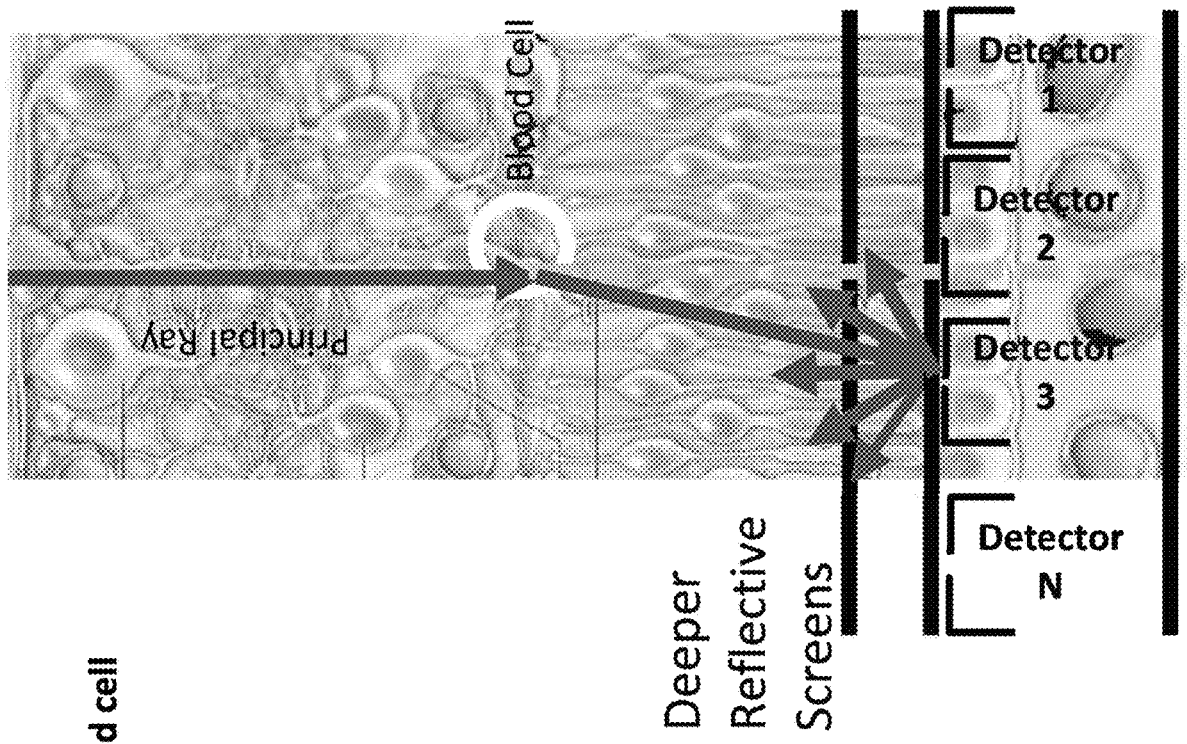
FIG. 15 is another drawing showing detection of light from a conjugate backscatter plane.

FIG. 15 is another drawing showing detection of light from a conjugate backscatter plane. FIG. 15 shows a detail of light travel through a blood cell that continues forward propagation of light.

Reflection at a deeper screen contains information about the cell contents, scatter, refractive index and other useful information regarding cell type.

Figure 16:
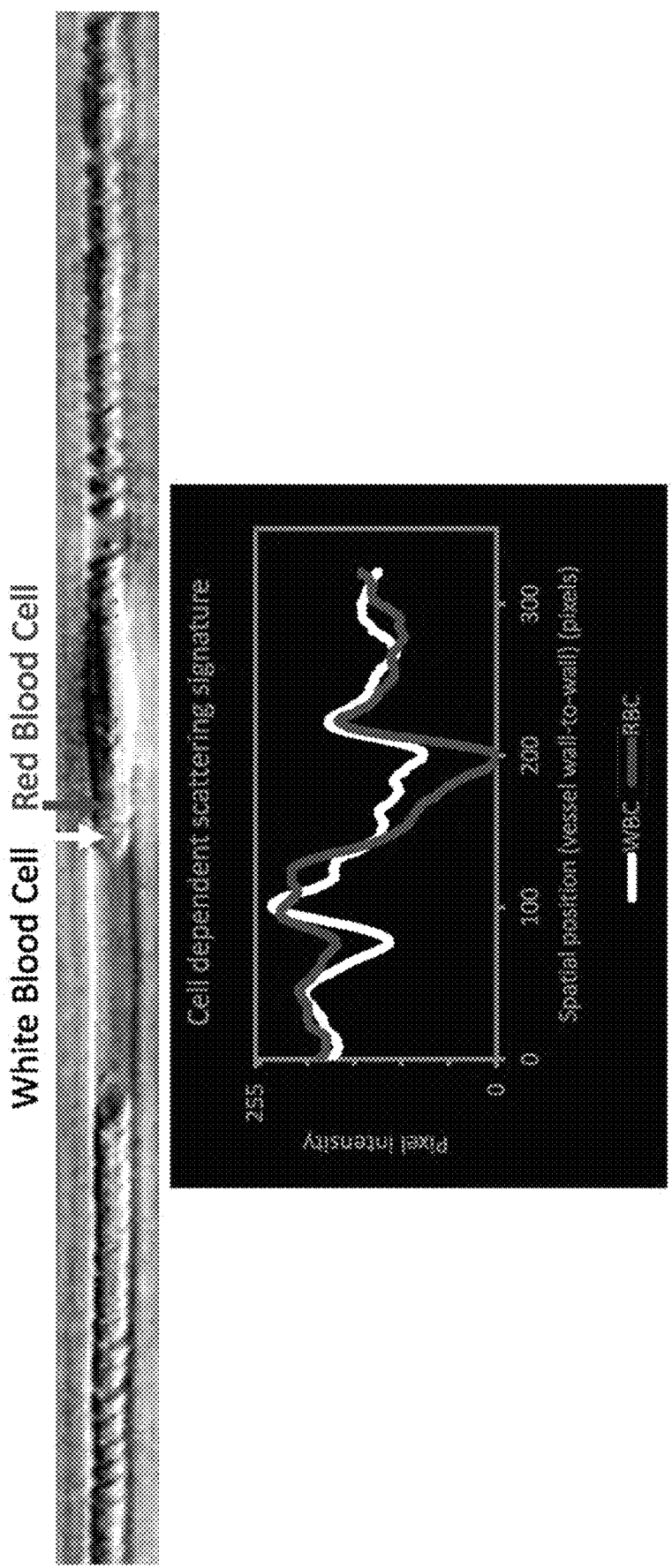
FIG. 16 is a drawing showing differences between light scattered by white and red blood cells.

FIG. 16 is a drawing showing differences between light scattered by white and red blood cells. FIG. 16 shows real data captured with the approach that shows different scatter profiles when red and white blood cells are imaged. This information will be combined with the forward and side scatter information to reveal not only WBC/RBC types, but also can reveal different sub-population of white blood cells, platelets reticulocytes, circulating malignant cells and other endogenous and exogenous bodies in whole blood.

Figure 17:
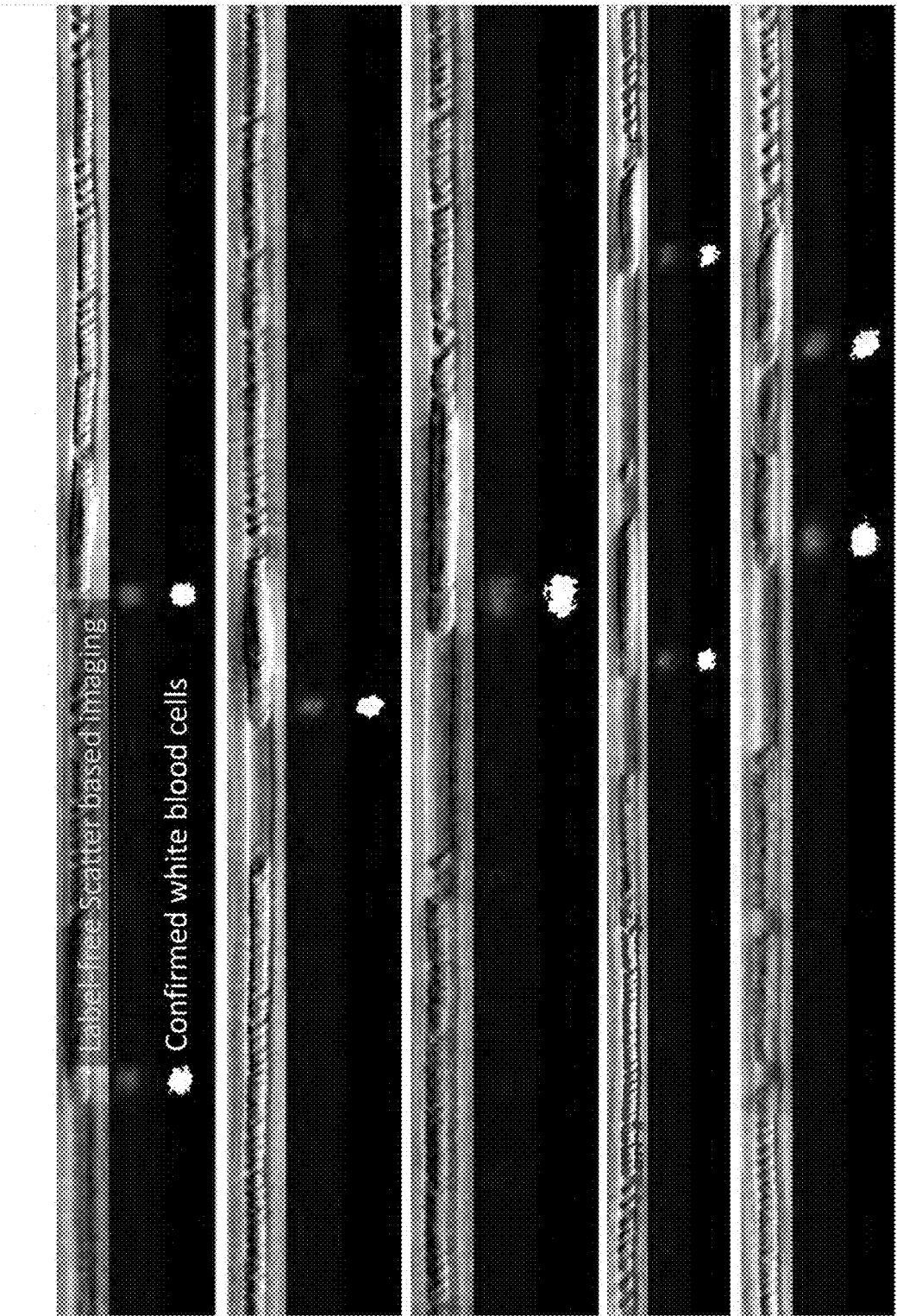
FIG. 17 is a drawing showing in vivo imaging of white blood cells in the absence of any contrast agent or labeling.

FIG. 17 is a drawing showing in vivo imaging of white blood cells in the absence of any contrast agent or labeling. FIG. 17 shows real data captured with the approach that confirms that white blood cells can be differentiated from red blood cells based on scatter profile alone.

REFERENCES for part 2, blood cell identification using comparisons of scatter in single and double pass light in the living retina Guevara-Torres, A., Joseph, A. & Schallek, J. (2016) Label free measurement of retinal blood cell flux, velocity, hematocrit and capillary width in the living mouse eye. Biomed. Opt. Express, BOE 7, 4228-4249 (2016). PMID-27867778

2. Guevara-Torres A, Williams DR, Schallek J. (2015) Imaging translucent cell bodies in the living mouse retina without contrast agents. Biomedical Optics Express.6(6): 2106-2119. doi: 10.1364/BOE.6.002106. PMID-26114032.

Part 3—Optimizing Translucent Cell Contrast in Adaptive Optics Ophthalmoscopy

Offset aperture and split-detection are techniques recently described in ophthalmoscopy that have optimized the visualization of translucent retinal structures [1-7]. Combined with adaptive optics that measure and correct for the aberrations of the eye, these non-confocal methods have demonstrated new abilities to directly image red blood cells, horizontal cells, ganglion cells along with photoreceptor inner segments and somas without contrast agents. Despite the recent utility of these approaches in the eye, models to explain the optical phenomena that provide cellular contrast in such configurations are incomplete.

One model presented by Elsner and Chui attributes the optical contrast to forward and multiple scatter [1,6]. In this model, illumination light that strikes the target object is forward scattered into deeper retinal layers which then is backscattered to the detector. This model is supported by evidence of improved contrast when the target object is above a highly reflective layer, such as in the optic disc [1]. This model based on forward scattered light which does not explain the contrast asymmetries characteristic of the offset aperture condition. In such images, one edge of the target object looks bright whereas the opposite edge appears dark giving the appearance of a three dimensional physical relief. Sulai et al. also observed contrast asymmetries using the split-detection configuration which compares light on either side of central optical axis [7], though the mechanism of contrast was not explained.

Building on this work, and guided by our own observations [3,4] we have realized an optical model at the cellular level that describes a biophysical source of this contrast. The refractive index of single cells and sub-cellular features may act as tiny lenses that steer light away from the optical axis in a direction consistent with the power of that cellular lens.

In this model of the Application, the forward propagated light is thus deviated away from the optical axis and forms a decentered point spread function (PSF) on a deeper reflective layer. In the retina, the photoreceptor, retinal pigment epithelium (RPE), choroid and scleral complex have a relatively higher amount of backscatter and serve as a deeper reflective screen [8-10]. In our new model of cellular refraction, we posit that the optimum configuration to maximize contrast is not only to laterally offset the aperture from the confocal center, but also to axially position the detection plane conjugate with the optimum backscatter plane as opposed to the target object to be imaged (the convention in current split-detection and offset aperture imaging).

To test our optical model, we used the living mouse eye as an advantageous system. The mouse has a numerical aperture of 0.49, twice that of the human, providing a two-fold increase in lateral resolution and a four-fold increase in axial resolution [10]. Lateral resolution has been theoretically and experimentally demonstrated to achieve ~700 nm lateral resolution [10]. The high NA also provides tight axial illumination confinement. The size of the axial point spread function (PSF), theoretically 9 μm [11], is comparable to the size of many retinal cell bodies. Correspondingly, this high NA provides a narrow depth-of-field. Light only ten micrometers deeper or shallower is appreciably defocused thereby enhancing contrast to a tiny axial volume of best focus. This is an advantageous property of the mouse eye which has remarkable optical power (560 diopters [12]). In addition to the optical benefits of the mouse eye, use of anesthesia provides a stable preparation that mitigates eye motion and impact of pupil centration that makes human investigation challenging.

Figure 18:
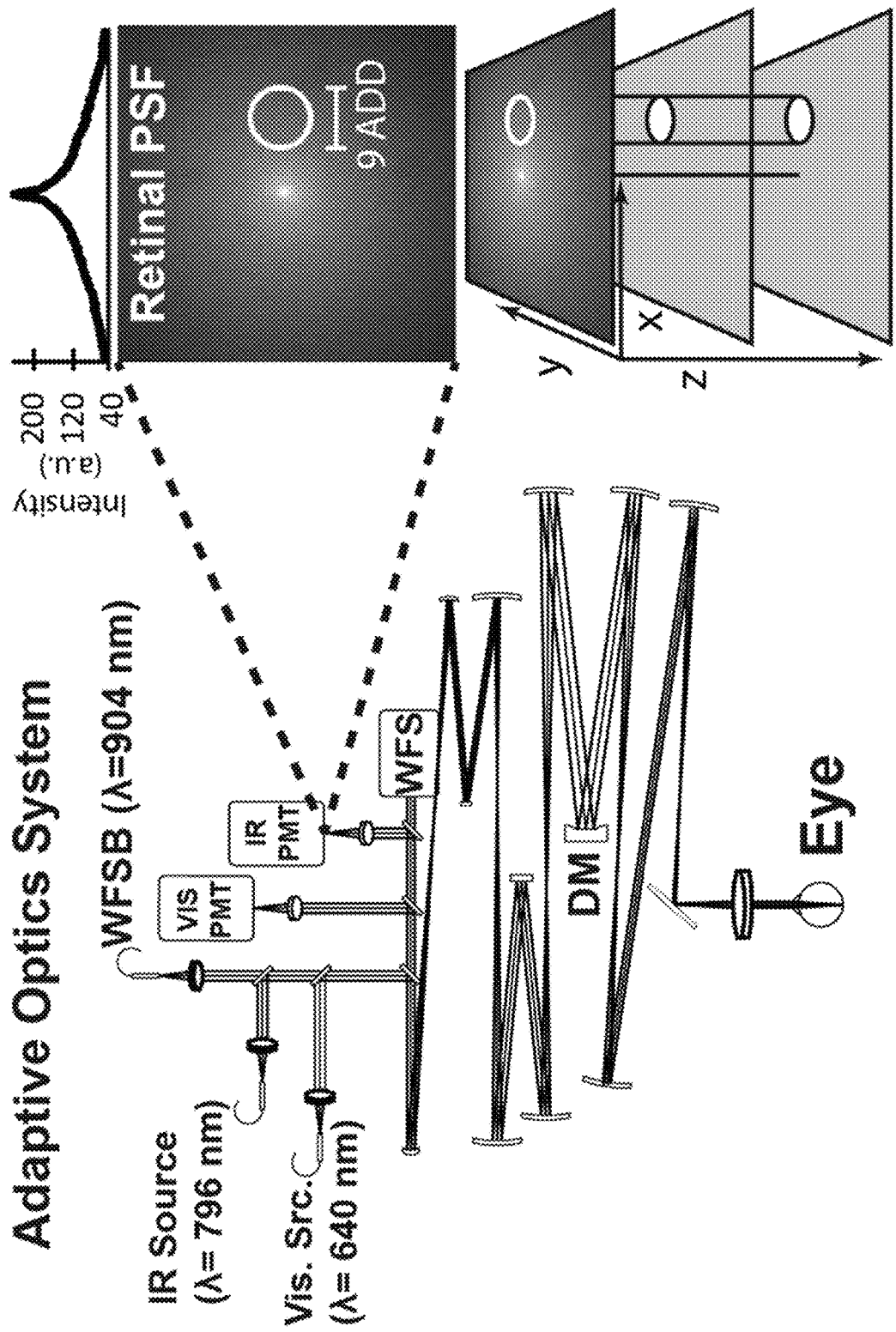
FIG. 18 is a system diagram of the AOSLO used in testing a configuration and method according to the Application.

FIG. 18 is a system diagram of the AOSLO used in testing a configuration and method according to the Application. Three light sources were used to provide imaging light at 796 and 640 nm and wavefront sensing at 904 nm. The wavefront sensor (WFS) provided aberration measurement while the deformable mirror (DM) provided aberration correction. Light backscattered from the eye was de-scanned and imaged at a retinal conjugate plane (right). The average retinal PSF was imaged with a CCD camera revealing typical light distribution from all imaged point locations in a frame. The detection pinhole (200 µm) was then displaced laterally to the confocal center (offset configuration, x=233-815 µm, or 10-35 ADD, y=0 µm.) Image contrast was evaluated with axial detector locations from, z=0-22 mm, 215 µm in retina).

To test our model, we use an adaptive optics scanning light ophthalmoscope (AOSLO) designed to image the mouse retina [10]. In brief, we used a 904 nm (8 µW) laser for wavefront sensing and 796 nm light with 17 nm bandwidth (480 µW, Superlum, Ireland) and a 640 nm visible laser (30 µW, Toptica, Germany) for imaging. A Shack-Hartmann wavefront sensor was used to measure aberrations and a membrane based deformable mirror (ALPAO, France) provided correction for high and low order aberrations of the eye. The AOSLO is composed of five afocal telescopes that relay the pupil of the eye to the deformable mirror and the horizontal and vertical scanners (FIG. 18). This scanning instrument has a frame rate of 25 Hz and a fast scanner frequency of 15.4 kHz. The imaging path (return path from the eye) de-scans and reimages a spot at the retina into the detector arm, generating an accessible PSF (FIG. 18). To test our model, we sample the PSF by moving a photomultiplier tube (PMT) with a coupled circular pinhole in both the lateral and axial dimensions. The actual PSF of the imaging arm (FIG. 18) was imaged using a CCD camera in the traditional PMT location (640×480 monochrome DMK21F04, The Imaging Source. Exposure 1/2048 seconds).

Similar to approaches by Sulai, Chui, Rossi and Guevara [1,3,5,7], the first step was to displace the detector pinhole laterally in the in the en face plane. The diameter of the detector aperture was 200 µm (equal to 9 Airy Disc Diameters (ADD) FIG. 18). The aperture was decentered in the horizontal dimension by 10 ADD for vessels, 22 and 35 ADD for experiments imaging horizontal cells. These decentered configurations were chosen to provide a baseline visualization of the object.

To test the impact of axial displacement of the detector, the lateral offset of the detector remained fixed while the aperture/PMT was systematically moved from the conjugate illumination plane of the imaged object to layers progressively deeper in the retina (more sclerad). For each experiment, the illumination and adaptive optics correction were held constant while detection configuration was varied. Maxwell's elongation formula provided the relationship between an axial displacement of the detector and its corresponding displacement at the retina. [11]

$$m_a = \frac{n'}{n} m^2 \qquad (1)$$

Here m is the lateral magnification n and n' are the indices of refraction at the eye and the detector. The Airy disc diameter at the detector is 23.3 µm and at the mouse retina is 2 µm. Then, assuming an index of refraction of 1.334 of the anterior eye, an axial displacement of 1 mm at the detector corresponds to an axial displacement of 9.8 µm in the retina. The detector position was moved up to 22 mm corresponding to over 215 µm of axial defocus in the retina. The alignment of the PMT mechanical stage had a lateral deviation of less than 1 ADD (23 µm) over the tested optical z-displacements. This tolerance was important and was confirmed using a CCD camera to calculate the center of the PSF along the 22 mm throw of the axial detector positions.

To correct for small residual motion within the mouse eye, a second 640 nm laser was used to simultaneously image the retina in confocal mode using a separate, visible light PMT (FIG. 18). This provided simultaneous, dual-channel image registration without impacting the measurements performed in the near infrared [13].

To quantify improvement, we imaged two classes of retinal structures: horizontal cells with diameter near ~11 micrometers [3]) and the smallest retinal capillaries with blood cells within (~4 micrometers [4]). These biological targets were chosen because they provide strong baseline contrast in the offset and split detector configurations [3,4] and reside vitread to the deeper reflective layers, whose impact we wish to assess. Retinal capillaries are further useful as they reside in three layers of the mouse retina, allowing the same structures to be imaged at different distances from the deeper reflective layers [14].

When imaging these objects in the offset configuration, we started with zero-axial offset (illumination is conjugate to detection plane). Images revealed cells and structures similar to those previously reported [1,3,5,7]. As the illumination remained fixed on the target object plane, the axial detector was moved deeper by 215 µm (38 diopters) in incremental steps (FIG. 19).

Figure 19B:
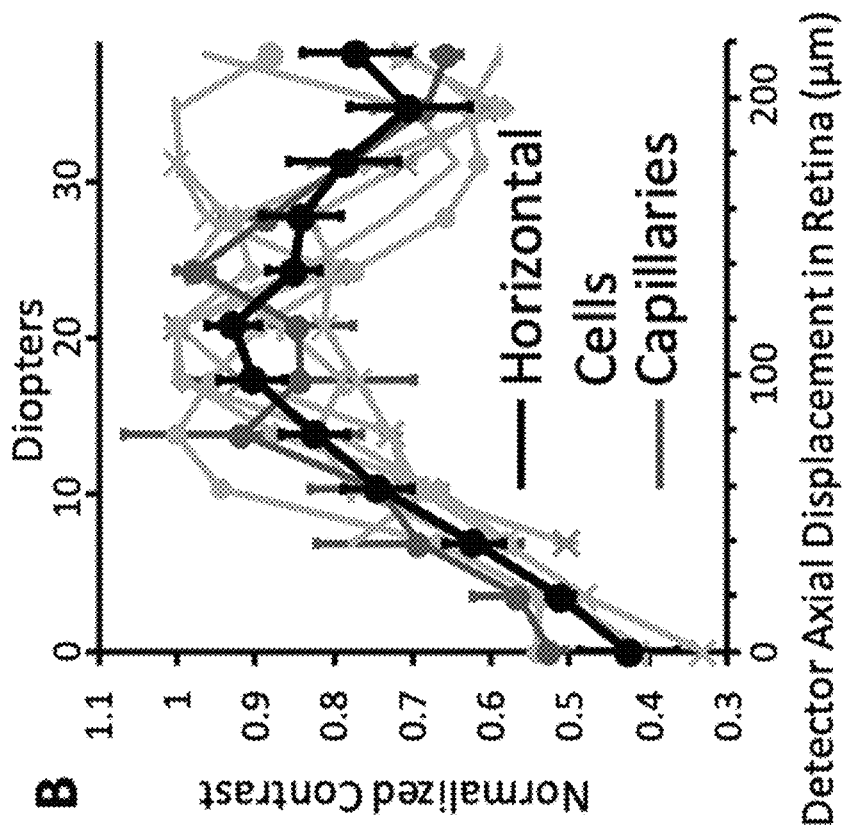
FIG. 19B is a graph showing a contrast improvement observed for all imaged cells.
Figure 19A:
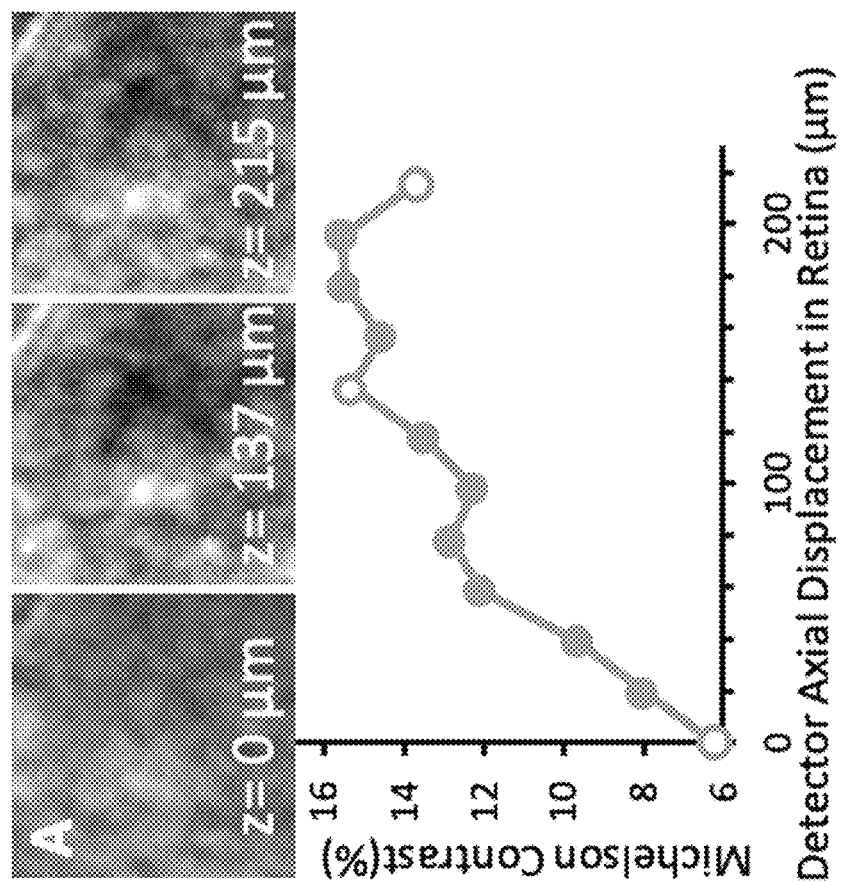
FIG. 19A is a series of images and a graph showing an increase in contrast from horizontal cells by axially displacing the detector.

FIG. 19A is a series of images and a graph showing an increase in contrast from horizontal cells by axially displacing the detector. Horizontal cell images are normalized to the mean intensity and displayed with the same contrast range (24×24 µm field of view). Michelson contrast for the cell above improves as detector is moved deeper (gray plot). FIG. 19B is a graph showing a contrast improvement was observed for all imaged cells (6 cells across 3 mice). The average plot for horizontal cells (black) shows a local maximum in the contrast at 117 µm. Capillaries at a similar anatomical depth as horizontal cells, (OPL) also show a local maximum at the similar detector position. The error bars represent standard error of the mean.

To analyze the effect of an axial displacement of the detector we first imaged horizontal cells that reside in a monolayer at the boundary of the inner nuclear layer (INL) and outer plexiform layer (OPL). Horizontal cells are sparsely distributed in the retina and may be modeled as a simplified cellular refractive element at the boundary of a heterogeneous plexiform layer [15]. Somewhat counterintuitive to traditional confocal theory, the same horizontal cell could be imaged despite moving the detector plane 38 diopters (215 µm) away from the illumination plane which was >20× larger than the axial illumination PSF (~9 µm). If direct backscatter alone provided contrast, any target object 38 diopters away would be virtually unrecognizable due to blur. Instead, when performing an axial displacement, not only did the same horizontal cell remained visible, but Michelson contrast increased on average 1.9×. By continuing the axial movement of the detector, a local maximum in the contrast was observed between 70 and 170 µm of displacement in the retina. The improvement in contrast was observed in 6 cells across 3 mice (FIG. 19B) and is anatomically consistent with the distance between horizontal cells and photoreceptor/RPE/choroid complex of the mouse. The refractive model predicts an advantage of axially displacing the detector conjugate to the photoreceptor/RPE layers. In such a configuration, the illumination PSF provides optical resolution and axial sectioning for the target object while the detector displacement optimizes contrast.

Figure 20:
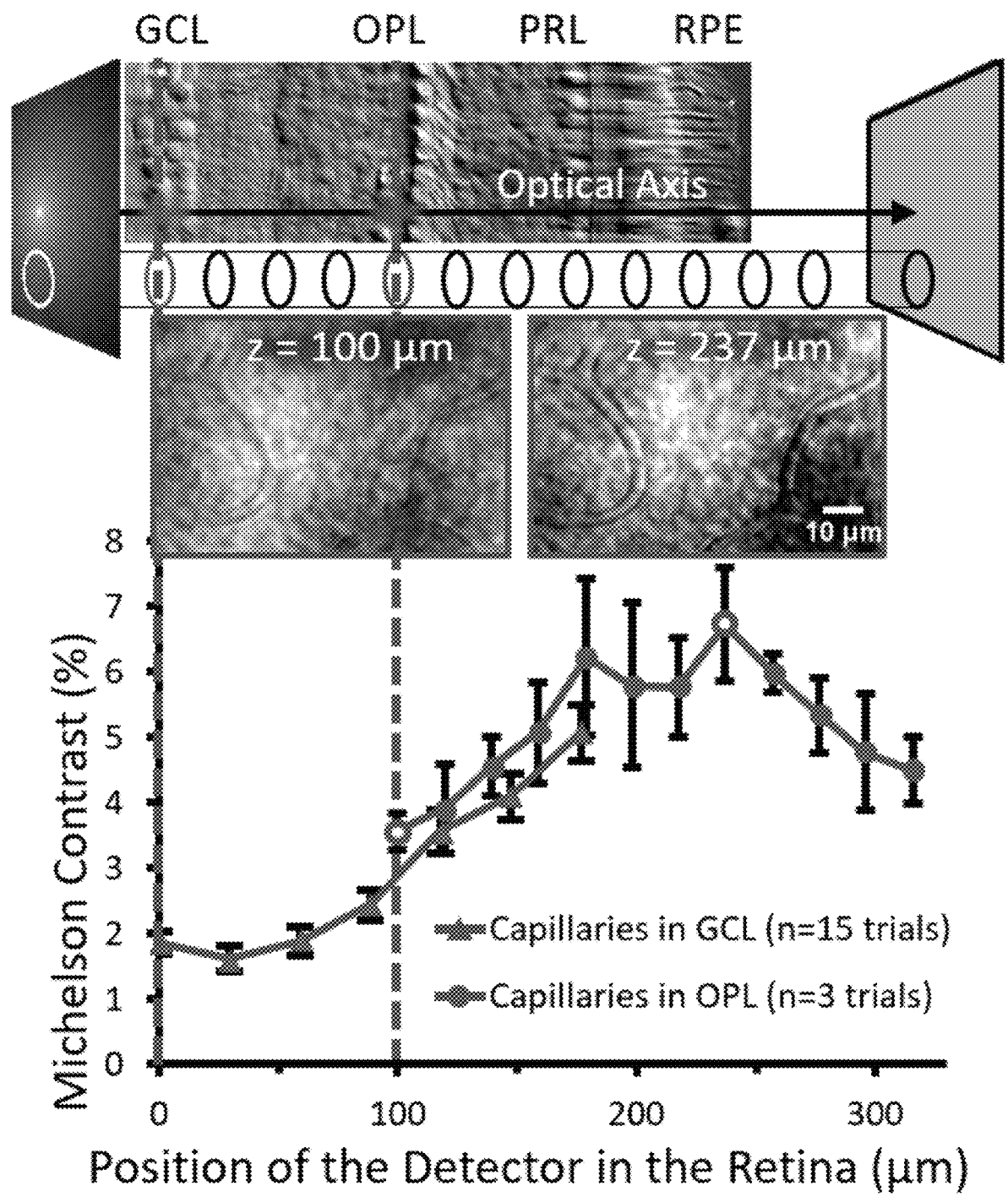
FIG. 20 is a series of images and a graph showing an improvement in image contrast by axially displacing the detector toward a layer of deeper retinal backscatter.

FIG. 20 is a series of images and a graph showing an improvement in image contrast by axially displacing the detector toward a layer of deeper retinal backscatter. Contrast increases with axial displacement regardless of whether vessels are in the GCL or OPL. A local maximum in contrast is observed when detector displacement is coincident with putative distance of the photoreceptor plane. 15 trials in GCL correspond to 7 imaged capillaries. 3 capillaries were imaged in the OPL. Axial image of retina provided by Stephen C. Massey (McGovern Medical School, UT Houston). The error bars show ±1 standard error of the mean.

To test that this was not a special case, true only for one type of structure in the retina, we also tested the effect in capillaries that are located in three stratifications in the mouse [14]. Capillaries at the ganglion cell layer (GCL) showed a continuous 2.7-fold increase in the contrast with the full range of our tested axial displacements (FIG. 20, curve lower left). To test if the optimum axial displacement depends on the distance between the target object and the photoreceptors, we also performed these experiments with capillaries at the OPL, which is closer to the reflective screen. When imaging capillaries at the OPL (FIG. 20, curve upper right) we observed an initial increase in the contrast consistent with the results from GCL capillaries. However, as the detector continued moving sclerad, we observed a contrast maximum 1.9× higher than when in the conjugate configuration. This maximum corresponded approximately at the plane of photoreceptor/RPE/choriocapillaris junction. This contrast maximum was similarly observed for horizontal cells residing at the same depth as the deepest retinal capillaries (FIG. 19B). These data suggest an optimal configuration for contrast is to align the detector plane with the reflective screen of greatest backscatter, and counterintuitively, not at the plane of the target object as is done in conventional confocal and offset imaging.

Figures 21A, 21B, 21C:
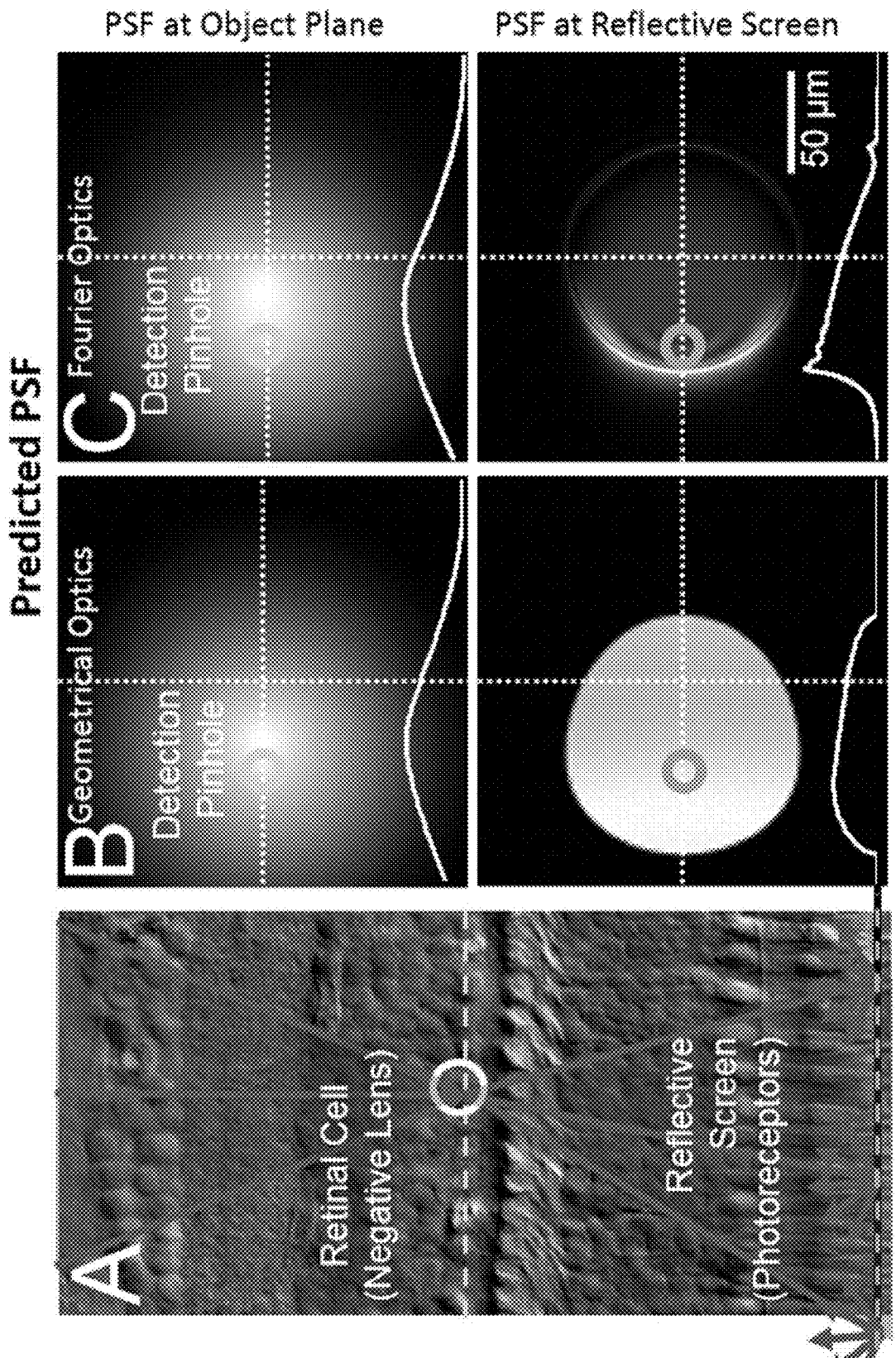
FIG. 21A is an image showing a cell acting as a negative lens deviates the rays that are focused on the left edge of the cell.
FIG. 21B is an image of a Zemax ray tracing which predicts the PSF pattern at a deeper screen when a lens is focused at the left of the cell (Below)
FIG. 21C is an image of a Zemax ray tracing using Fourier Optics.

FIG. 21A to FIG. 21C show an optical model describing the increase in the contrast. FIG. 21A is an image showing a cell acting as a negative lens deviates the rays that are focused on the left edge of the cell. This deviation is propagated to deeper reflecting layers like the photoreceptor/RPE complex. FIG. 21B is an image of a Zemax ray tracing using 3 million rays predicts the PSF pattern at a deeper screen when a lens is focused at the left of the cell (Below). When the detector is conjugate the focused beam and the cell of interest, defocus in introduced (above). FIG. 21C is an image of a Zemax ray tracing using Fourier Optics.

This improvement is predicted by our cellular refractive model by which single cells in the retina steer light to a deeper screen (FIG. 21A to FIG. 21C). By way of example, we consider a spherical cell diameter of 11 µm. Inside the cell was modeled with biological values as an index of 1.346, outside of the cell 1.400 providing an index mismatch of 1.04 creating a negative lens [16]. Illumination light was modeled as a cone of light coming from a pupil of 2 mm diameter [10]. The anterior optics of focal length of 2.38 mm with a wavelength of 796 nm was focused on a single spherical cell (FIG. 21A). From this cell, light was forward propagated to a deeper reflective screen such as the photoreceptors which reside 130 µm below the cell. [25]

The model was simulated using two conventions in optics. 1) geometrical raytracing software (Zemax, Kirkland, Wash.) shown in FIG. 21B and 2) Fourier Optics [17] in a custom MATLAB script (Natick, Mass.). In the Fourier case (FIG. 21C), the cell is expressed as a 2D phase object generated from the spherical cell and the refractive index mismatch. The cell at beam focus is illuminated by a diffraction limited PSF. The light that passes through travels to a deeper screen is calculated using a numerical Fraunhofer propagation. Results from five discrete wavelengths equally spaced from 787.5 to 804.5 nm were independently tested and combined.

The return of the light, from the deeper screen to the detector is displayed in two ways: A) When detector is conjugate to the screen, then a diffraction limited PSF was used assuming that the reflection from the deeper screen is diffuse, or B) When the detector was conjugate to the imaged object, defocus was introduced by convolving the light pattern at the screen with a geometrical PSF defined by the numerical aperture and the defocus distance.

These results are consistent with a model where contrast arises from cellular refractive index and in a simplified version, the results can be explained by cellular lensing [16,18]. The geometry plus the difference of refractive indices of cells and their surrounds create small lenses that deviate light traveling to deeper layers. When focused rays are scanned across a cell, the illuminating light is deviated from the optical axis in a direction consistent with the optical power of that cell. Rays passing through the left and right will be steered into opposite directions (FIG. 21A to FIG. 21C). In either case, the deviated rays strike layers beneath the cell that reflect the light towards the detectors. Lateral displacement of the detector from the confocal center, like in offset aperture and split-detection, favors light passing through one side of the cell relative to the other. In the case of either split-detection or offset aperture [3,5,7].

FIG. 21B shows the offset aperture configuration and FIG. 21C shows the split-detection configuration. Split-detection and offset aperture are detection schemes within a 2D plane. Before this Application offset aperture and split-detection were restricted to a plane conjugate to the plane of illumination as inspired by confocal theory. With a better understanding of the role of cellular refraction and variations of refractive index within the plane of illumination coupled with a deeper backscattering screen, this application proposed moving detection masks like offset aperture to other planes, such as, for example planes conjugate to deeper screens. Offset aperture and split detection are names for 2D binary detection masks using one or multiple detectors, however there is an infinite possibility for the shapes of these 2D masks.

Techniques of AOSLO detection were also described in detail in co-pending U.S. patent application Ser. No. 15/563,035, IMAGING MODALITIES USING A REFLECTIVE APERTURE ARRAY IN THE IMAGING PLANE TO DYNAMICALLY IMAGE AND COMPARE COMPONENTS OF THE DIFFRACTION PATTERN AND IMAGING POINT-SPREAD FUNCTION, and also assigned to the University of Rochester. The '035 application is incorporated herein by reference in its entirety for all purposes.

While reflection from retinal layers may be specular, previous studies have emphasized the role of diffuse backscatter [19]. Provided this interaction, the forward propagated light strikes the diffusive screen, at which point, it serves as an independent source of light. This light is biased to left or right of the optical axis based on the cellular refraction of light. To extract optical steering and maximize contrast, an optimal strategy is to place the detector conjugate to the screen (FIG. 21A to FIG. 21C) while the focused illumination is positioned at the target layer.

Figure 22A:
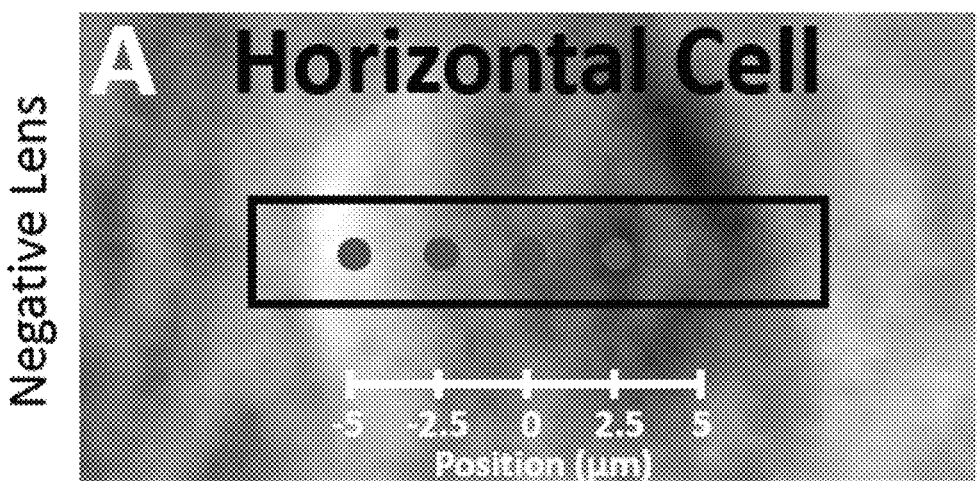
FIG. 22A is an image showing a horizontal cell (HC) imaged with split detection shows positive contrast at left, and negative contrast at right.
Figure 22B:
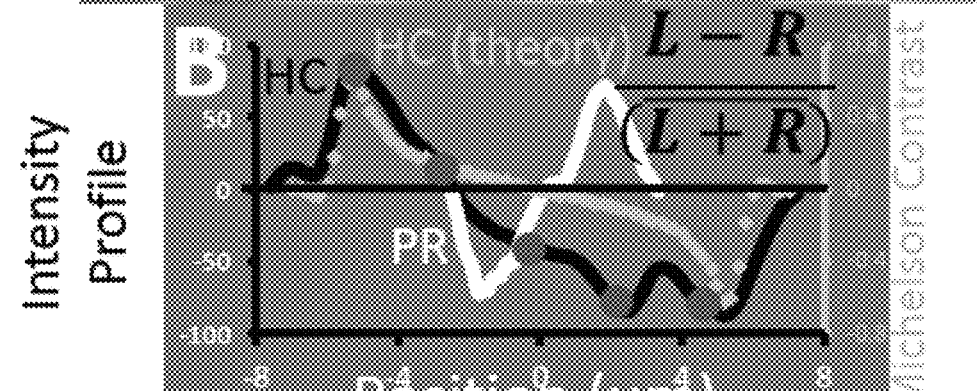
FIG. 22B is a graph showing an intensity profile across the imaged HC of FIG. 22A.
Figure 22C:
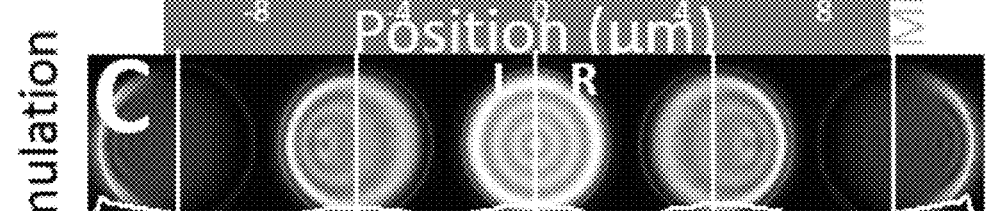
FIG. 22C is an image showing a simulated Fourier optics results at the detection plane.
Figure 22D:
FIG. 22D is an image showing photoreceptor (PR) somas captured with split-detection.
Figure 22E:
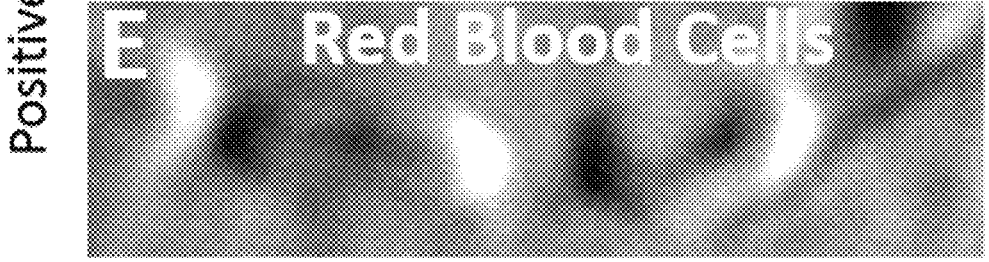
FIG. 22E is a split detection image of a red blood cell.

FIG. 22A to FIG. 22E are an exemplary model and data showing how differences in lens polarity can produce contrast of cells in split detector configuration. FIG. 22A is an image showing a horizontal cell (HC) imaged with split detection shows positive contrast at left, and negative contrast at right [3]. FIG. 22B is a graph showing an intensity profile across the imaged HC shown in FIG. 22A and simulated Fourier Optics data as in B in scan intervals of 0.2 µm. Each yellow point is a result from the simulation. The profile of the photoreceptor soma (PR) corresponding to (D) is shown in white. FIG. 22C is an image showing a simulated Fourier optics results at the detection plane as the bean is focused across the cell from −5 to 5 µm. FIG. 22D is an image showing photoreceptor (PR) somas captured with split-detection. FIG. 22E is a split detection image of a red blood cell.

A second prediction of cellular lensing is that each cell could act either as a positive or negative lens. This would change the steering angle of light on the deeper reflective screen. In this way, signal polarity is dictated by the index of refraction inside/outside the cell and the convex or concave nature of their geometry. In split-detection and offset aperture images, cells manifest as a dark shadow on one edge and a bright reflex on the other. We observe evidence of this phenomenon in our data, the left edge of the endothelium boundary is bright while the corresponding edge of red blood cells is dark. Photoreceptor somas and red blood cells have a predictive polarity of a positive lens. In blood cells, this is consistent with the higher index of refraction inside a red blood cell relative to plasma [20]. However, despite identical experimental conditions, horizontal cells and the capillary endothelium boundary have the polarity of a negative lens (FIG. 22).

To our knowledge, this is the first time that changes in cellular refractive index have been used to describe the asymmetries characteristic of split-detection and offset aperture images in ophthalmoscopy. This model implies that split-detection and offset aperture are ways to perform phase imaging in the living eye and the mechanism to generate contrast is analogous to Schlieren imaging, oblique illumination or differential phase contrast [21-23] where optical pathlength changes across the plane of focus deviate light in a particular direction.

There can be a detection mask that combines an optimized pattern, size, lateral and axial offset combinations to image specific cell types in the retina. Recent effort on this front comes from Sapoznik et al. who showed feasibility and benefits of an adaptable detection mask [24]. At the same time, our raytracing and Fourier Optics simulations can be used to instruct the best aperture configurations. Our model with the knowledge of the distance to the screen, size, geometry and refractive properties of each retinal cell type can provide an instructed detector mask for each cell class.

Because this approach does not require contrast agents, these strategies can be transferred to a human AOSLO to optimize detector configurations consistent with the size, refractive index and geometry of the human eye. Beyond generating contrast in translucent cells, this configuration can provide a unique biomarker to report the functional state of neurons and capillaries in the retina. Changes in both cell shape and refractive index may steer the beam in a favorable way to produce a biomarker of cell activity. Also, detection of the PSF deviation and shape can reveal the activity of the target cell.

REFERENCES for Part 3, Optimizing Translucent Cell Contrast in Adaptive Optics Ophthalmoscopy 1. T. Y. P. Chui, D. A. VanNasdale, and S. A. Burns, "The use of forward scatter to improve retinal vascular imaging with an adaptive optics scanning laser ophthalmoscope," Biomed Opt Express 3, 2537-2549 (2012).
2. D. Scoles, Y. N. Sulai, C. S. Langlo, G. A. Fishman, C. A. Curcio, J. Carroll, and A. Dubra, "In Vivo Imaging of Human Cone Photoreceptor Inner Segments," Invest. Ophthalmol. Vis. Sci. 55, 4244-4251 (2014).
3. A. Guevara-Torres, D. R. Williams, and J. B. Schallek, "Imaging translucent cell bodies in the living mouse retina without contrast agents," Biomed Opt Express 6, 2106-2119 (2015).
4. A. Guevara-Torres, A. Joseph, and J. B. Schallek, "Label free measurement of retinal blood cell flux, velocity, hematocrit and capillary width in the living mouse eye," Biomed. Opt. Express 7, 4228-4249 (2016).
5. E. A. Rossi, C. E. Granger, R. Sharma, Q. Yang, K. Saito, C. Schwarz, S. Walters, K. Nozato, J. Zhang, T. Kawakami, W. Fischer, L. R. Latchney, J. J. Hunter, M. M. Chung, and D. R. Williams, "Imaging individual neurons in the retinal ganglion cell layer of the living eye," Proc. Natl. Acad. Sci. 114, 586-591 (2017).
6. A. Elsner, M. Miura, S. Burns, E. Beausencourt, C. Kunze, L. Kelley, J. Walker, G. Wing, P. Raskauskas, D. Fletcher, Q. Zhou, and A. Dreher, "Multiply scattered light tomography and confocal imaging: detecting neovascularization in age-related macular degeneration," Opt. Express 7, 95-106 (2000).
7. Y. N. Sulai, D. Scoles, Z. Harvey, and A. Dubra, "Visualization of retinal vascular structure and perfusion with a nonconfocal adaptive optics scanning light ophthalmoscope," J. Opt. Soc. Am. A 31, 569-579 (2014).
8. R. H. Webb, G. W. Hughes, and F. C. Delori, "Confocal scanning laser ophthalmoscope," Appl. Opt. 26, 1492-1499 (1987).
9. J. Van de Kraats, T. T. J. M. Berendschot, and D. Van Norren, "The Pathways of Light Measured in Fundus Reflectometry," Vision Res. 36, 2229-2247 (1996).
10. Y. Geng, A. Dubra, L. Yin, W. H. Merigan, R. Sharma, R. T. Libby, and D. R. Williams, "Adaptive optics retinal imaging in the living mouse eye," Biomed. Opt. Express 3, 715-734 (2012).
11. M. Born and E. Wolf, Principles of Optics: Electromagnetic Theory of Propagation, Interference and Diffraction of Light, 7th (expanded) edition (Cambridge University Press, 2002).
12. S. Remtulla and P. E. Hallett, "A schematic eye for the mouse, and comparisons with the rat," Vision Res. 25, 21-31 (1985).
13. A. Dubra and Z. Harvey, "Registration of 2D Images from Fast Scanning Ophthalmic Instruments," in Biomedical Image Registration, Lecture Notes in Computer Science No. 6204 (Springer Berlin Heidelberg, 2010), pp. 60-71.
14. R. A. Cuthbertson and T. E. Mandel, "Anatomy of the mouse retina. Endothelial cell-pericyte ratio and capillary distribution.," Invest. Ophthalmol. Vis. Sci. 27, 1659-1664 (1986).
15. M. D. Fischer, G. Huber, S. C. Beck, N Tanimoto, R. Muehlfriedel, E. Fahl, C. Grimm, A. Wenzel, C. E. Remé, S. A. van de Pavert, J. Wijnholds, M. Pacal, R. Bremner, and M. W. Seeliger, "Noninvasive, In Vivo Assessment of Mouse Retinal Structure Using Optical Coherence Tomography," PLoS ONE 4, e7507 (2009).

16. M. Kreysing, L. Boyde, J. Guck, and K. J. Chalut, "Physical insight into light scattering by photoreceptor cell nuclei," Opt. Lett. 35, 2639-2641 (2010).
17. J. W. Goodman, Introduction to Fourier Optics, 3rd ed. (Roberts & Company, 2005).
18. B. Vohnsen, "Directional sensitivity of the retina: A layered scattering model of outer-segment photoreceptor pigments," Biomed. Opt. Express 5,1569-1587 (2014).
19. G. J. Van Blokland and D. Van Norren, "Intensity and polarization of light scattered at small angles from the human fovea," Vision Res. 26,485-494 (1986).
20. A. G. Borovoi, E. I. Naats, and U. G. Oppel, "Scattering of Light by a Red Blood Cell," J. Biomed. Opt. 3, 364-372 (1998).
21. T. N. Ford, K. K. Chu, and J. Mertz, "Phase-gradient microscopy in thick tissue with oblique back-illumination," Nat. Methods 9, 1195-1197 (2012).
22. L. Joannes, F. Dubois, and J.-C. Legros, "Phase-shifting schlieren: high-resolution quantitative schlieren that uses the phase-shifting technique principle," Appl. Opt. 42, 5046-5053 (2003).
23. D. K. Hamilton and C. J. R. Sheppard, "Differential phase contrast in scanning optical microscopy," J. Microsc. 133, 27-39 (1984).
24. K. A. Sapoznik, T. Luo, A. de Castro, L. Sawides, R. L. Warner, and S. A. Burns, "Enhanced retinal vasculature imaging with a rapidly configurable aperture," Biomed. Opt. Express 9, 1323-1333 (2018).
25. K. H. Kim, M. Puoris'haag, G. N. Maguluri, Y. Umino, K. Cusato, R. B. Barlow, and J. F. de Boer, "Monitoring mouse retinal degeneration with high-resolution spectral-domain optical coherence tomography," J. Vis. 8, 17-17 (2008).

Part 4—Adaptive Optics Permits Label-Free Intravital Imaging of Dynamic Immune Responses in The Retina Adaptive-optics infra-red reflectance imaging permits label-free and environmentally unperturbed imaging of infiltrating and resident immune cells within the inner retina of the mouse eye at sub-cellular resolutions. Following inflammatory stimulus, the entire immune response can be recapitulated and tracked across minutes to months repeatedly at the same anatomical location.

Due to the noninvasive nature and the safe light levels used, comparable human imaging during ocular inflammation can detect motile structures consistent with immune cells, a finding that can greatly advance the study of immunity and eye disease.

The eye is optimally suited to image immune responses. As the only optically transparent organ in mammals it requires no surgical or environmental perturbation to access, providing the highest fidelity platform for repeated visualization of true immune system function in vivo. [1] Limitations in attaining intravital single-cell resolution and the requirement for cell labelling however in both mouse and man have impeded wider application to the study of fundamental immunology or blinding diseases.

To address these issues, a scanning laser ophthalmoscope incorporating adaptive optics correction (AOSLO) was deployed to image the mouse eye. Using real-time rectification of higher order optical aberrations, this approach has previously achieved single-cell resolution from retinal photoreceptors to intravascular erythrocytes. [2,3] Reflectance imaging with 796 nm infrared light also detects retinal structure allowing repeated navigation to the same location.

The following examples were made using the new method and detector configuration of the Application.

Figure 23:
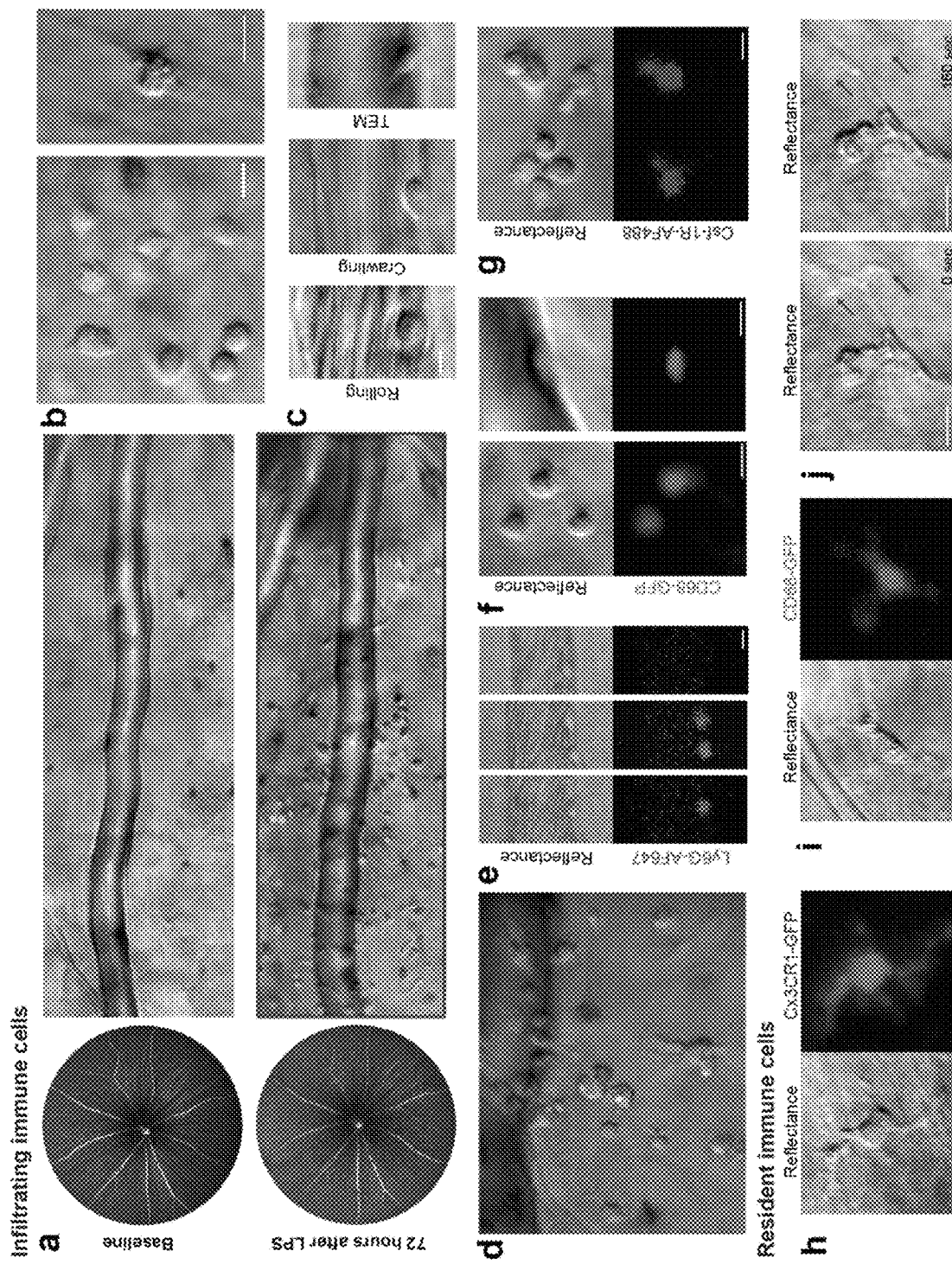
FIG. 23A is an image showing a 796 nm reflectance, widefield 55 degree SLO of infiltrating immune cells with an indicated location (rectangle) of an adjacent AOSLO montage at baseline and at 72-hours post LPS.
FIG. 23B is an image showing heterogenous cell types visualized by 796 nm reflectance, 24-hours post LPS.
FIG. 23C is an image showing intravascular single-cell reflectance images across range of transendothelial migration including rolling, crawling, and TEM.
FIG. 23D is an image showing an intermediate magnification field with retinal vein above, 72 hours post LPS.
FIG. 23E is an image showing an anti-Ly6G antibody labelled leukocyte rolling, 6 hours-post LPS.
FIG. 23F is an image showing a CD68-GFP reporter mouse with cells in tissue and intravascular crawling, 24 hours post LPS.
FIG. 23G is an image showing a Representative examples of naïve retinal microglia in FIG. 23H, Cx3cr1-GFP.
FIG. 23H is an image showing Cx3cr1-GFP.
FIG. 23I is an image showing CD68-GFP reporter mice.
FIG. 23J is an image showing a reflectance image of a spontaneous second-order microglial process retraction at 0 sec and 160 sec.
Figure 24:
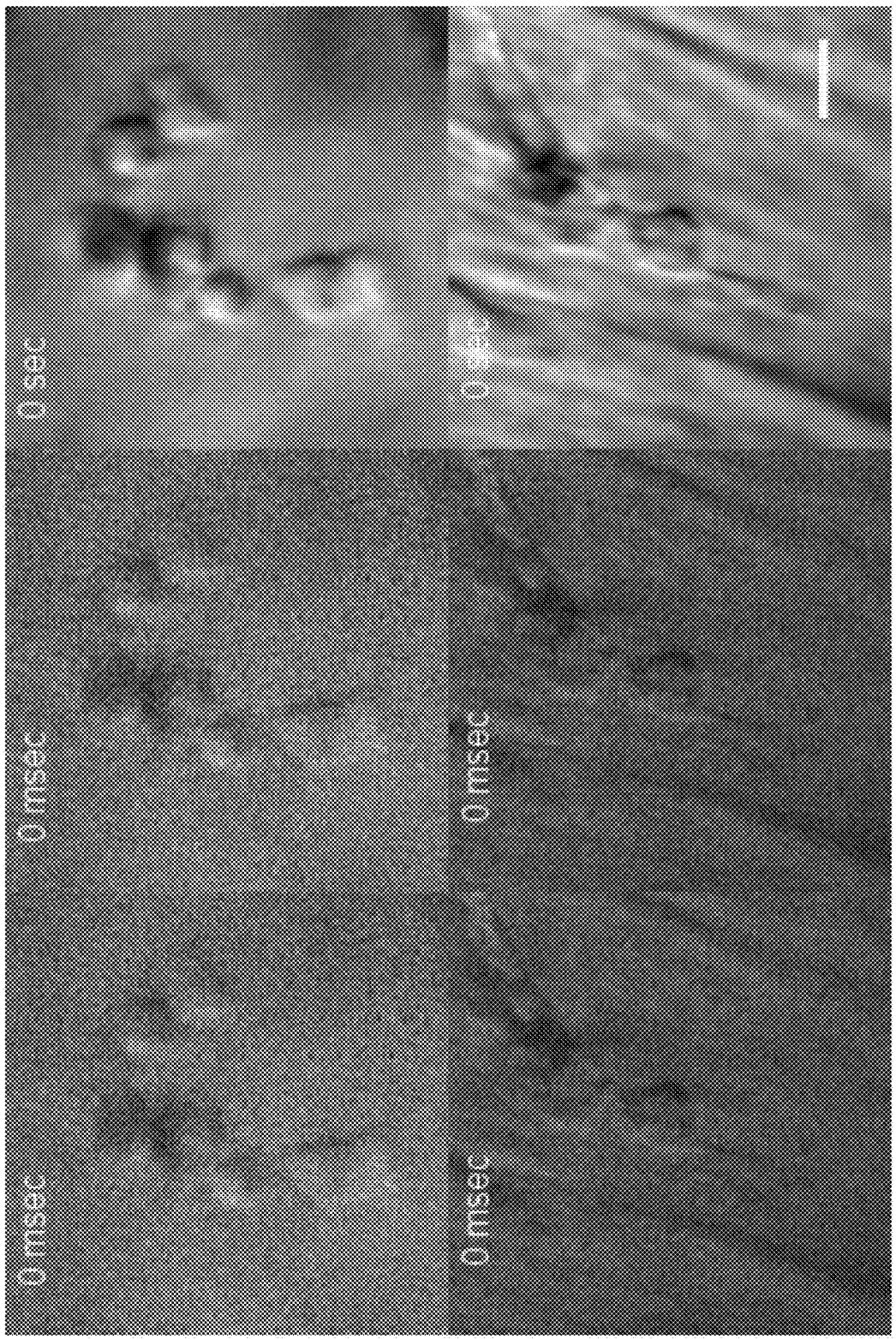
FIG. 24 is a series of still images representing a registration and processing video.
Figure 26:
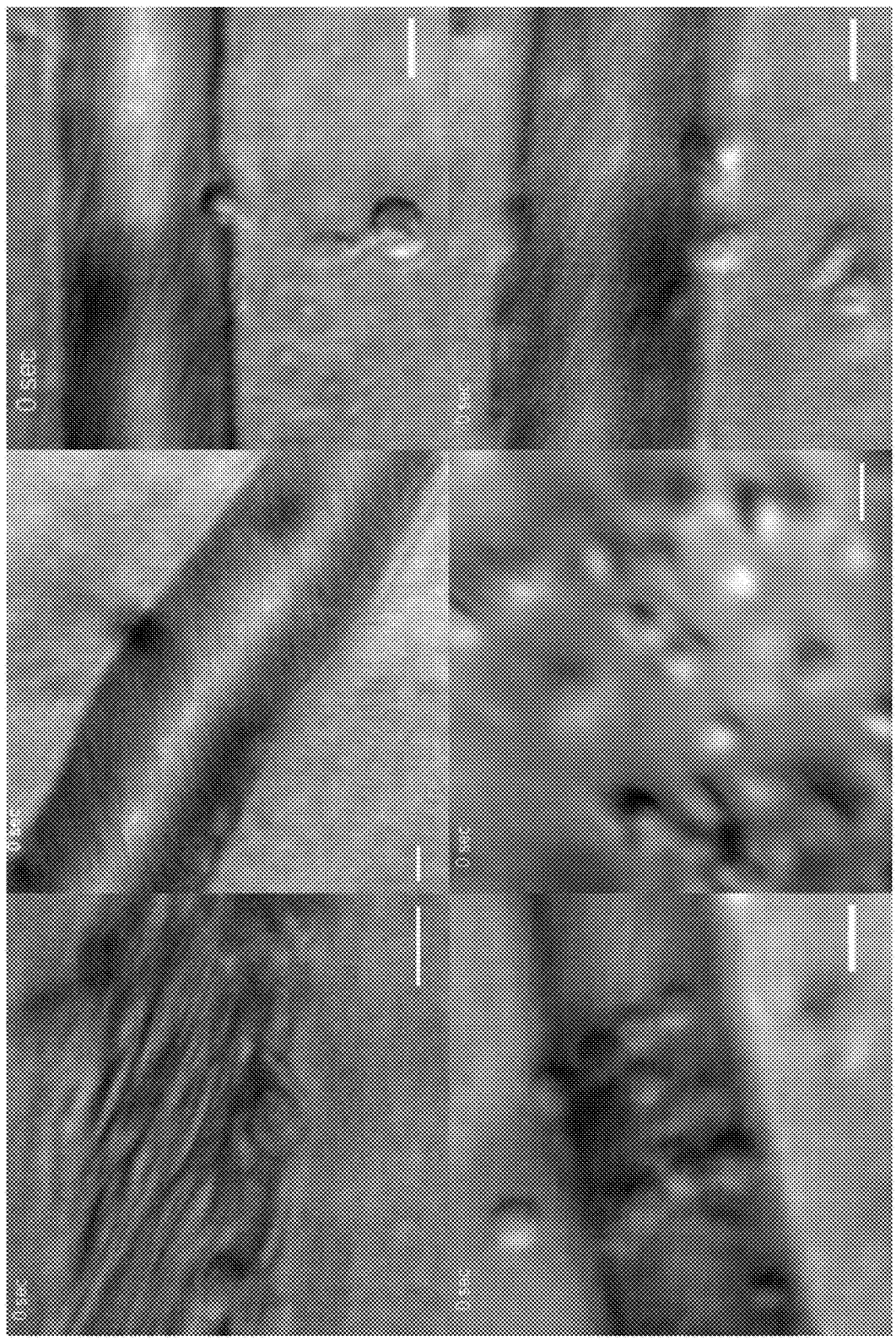
FIG. 26 is a series of still images representing a TEM reverse migration, montage of types of movement video.

A single acute inflammatory stimulus was delivered by intravitreal injection of lipopolysaccharide (LPS), known to result in retinal recruitment of myeloid cells, resolving through efferocytosis by seven days. [4] Reflectance changes developed around retinal veins (FIGS. 23A-J) and were best observed when incorporating an offset-aperture detection strategy akin to side-scatter in flow cytometry. [5] Discrete structures within inner retinal tissue appeared static when visualized in real-time, until post-processing with image registration, frame averaging and accelerated time-lapse video (FIG. 24). This revealed dynamic membrane remodeling, pseudopodia formation and cell motility consistent with infiltrating immune cells (FIG. 23B, FIG. 24). Viewing post-capillary venules, reflectance imaging could identify leukocyte rolling, crawling, transendothelial and reverse migration behaviors (FIG. 23C, FIG. 26). Heterogeneity in cell location, size, internal reflectivity and motility can be observed over wide regions of tissue, with multiple cell types in different stages of direct interaction (FIG. 23D).

FIGS. 23A-J are images showing infiltrating immune cells (FIGS. 23A-G) and resident immune cells (FIG. 23H-FIG. 23J). Label-free adaptive optics imaging of retinal immune cells are shown as: FIG. 23A, 796 nm reflectance, widefield 55-degree SLO with indicated location (red rectangle) of adjacent AOSLO montage. FIG. 23B, heterogenous cell types visualized by 796 nm reflectance, 24-hour post LPS. FIG. 23C, Intravascular single-cell reflectance images across range of transendothelial migration. FIG. 23D, Intermediate magnification field with retinal vein above, 72 hours post LPS. Representative examples of simultaneous reflectance (above) and fluorescence (below) for FIG. 23E, anti-Ly6G antibody labelled leukocyte rolling, 6 hours-post LPS and FIG. 23F, CD68-GFP reporter mouse with cells in tissue and intravascular crawling, 24 hours post LPS. FIG. 23G. Representative examples of naïve retinal microglia in FIG. 23H, Cx3cr1-GFP and FIG. 23I, CD68-GFP reporter mice. FIG. 23J, Reflectance image of spontaneous second-order microglial process retraction. Scale bars =10 µm, except in a=X µm. 0.9 Gaussian Filter applied to fluorescence images.

The ocular infiltrate secondary to LPS injection is almost exclusively neutrophil or monocyte derived. [4] Simultaneous single-channel fluorescence detection is possible with this AOSLO, so intravascular staining with conjugated anti-Ly6G antibody was used to verify the majority of endothelial rolling were neutrophils (FIG. 23E, FIG. 27). [6] Using CD68GFP/+ reporter mice, intravascular monocytes and macrophages within retinal tissue could also be identified (FIG. 23F).

Figure 28:
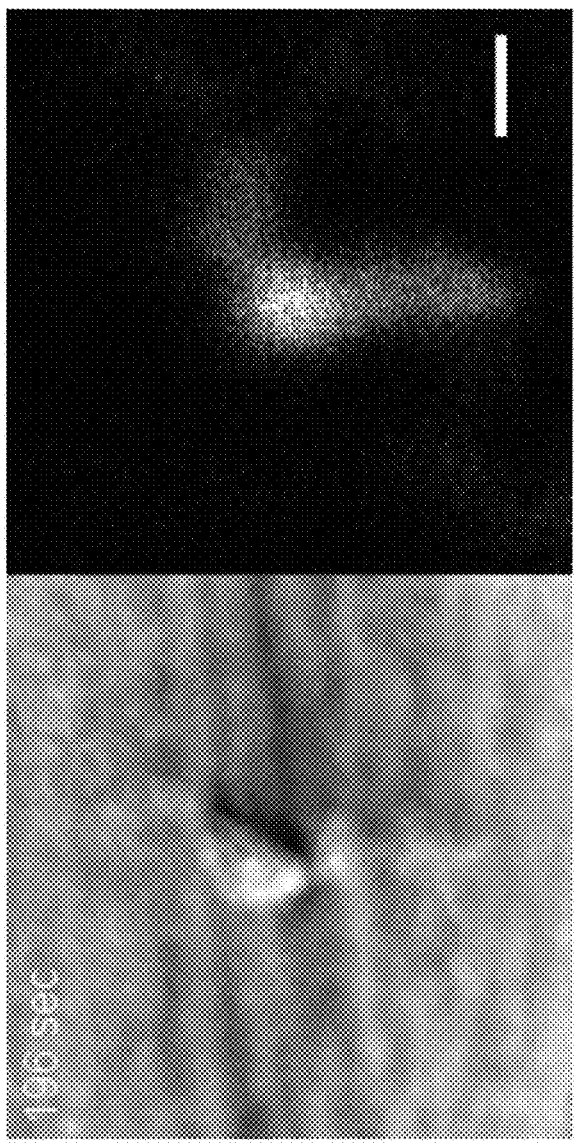
FIG. 28 is a series of still images representing a video of microglia plus dynamic processes.

To ascertain if resident immune cells could be visualized, uninflamed eyes were imaged and high reflectance dendriform structures could be observed from vitreous cavity to the ganglion cell layer, distinct from expected neuronal constituents. These were identified as retinal microglia by positive fluorescence co-localization in Cx3cr1GFP/+ and CD68GFP/+ reporter mice (FIG. 23H-FIG. 23I). Resolution to a minimum of second-order dendritic processes was possible (FIG. 23J, extended data FIG. 29) with dynamic motility recordable in real-time (FIG. 28). Additionally, resolution of subcellular details was possible consistent with structures such as endosomes as previously identified in this population (Extended data FIG. 30). [7]

Extended Data

FIG. 24 is a series of still images representing a registration and processing video; Extended Data Video 1. Demonstration of post-processing application. a. Raw adaptive optics corrected 796 nm reflectance image of C57BL/6J mouse retina. Real-time video obtained at 25 fps acquisition demonstrating movement from respiration and cardiac output. b, Raw Image following frame-registration by EyeTrack software. c, Application of 25 frame temporal averaging and accelerated time-lapse. Top row, cluster of infiltrated immune cells 6 hours post-LPS. Bottom row, tissue resident cell in uninflamed retina. Scale bars=10 µm.

Figure 25:
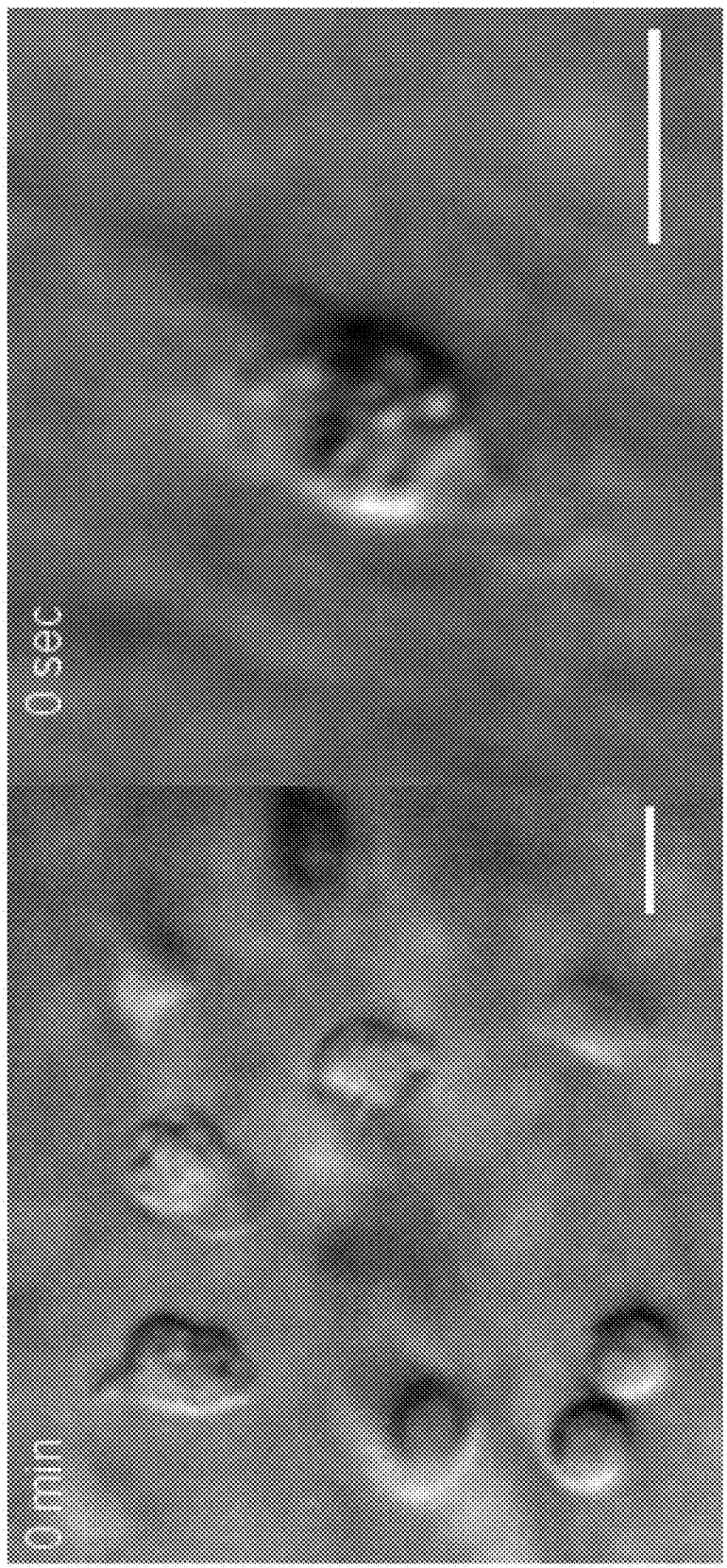
FIG. 25 is a series of still images representing a video of cells moving (FIG. 23B) frame.

FIG. 25 is a series of still images representing a video of cells moving (FIG. 23B) frame; Extended Data Video 2. Label-free AOSLO time-lapse video demonstrating heterogenous Immune cell motility. 796 nm reflectance video acquired at 25 fps from C57BL/6J mouse retina 24 hours post LPS injection. Post-processed and 50 frame temporal averaging from total 6-minute duration recording. Scale bars=10 µm.

FIG. 26 is a series of still images representing a TEM reverse migration, montage of types of movement video; Extended Data Video 3. Examples of diverse cell behavior observed by AOSLO reflectance imaging. 796 nm reflectance AOSLO images at 6 or 24 hours post-LPS between 5 to 50 frame averaging. a, post-capillary venule leukocyte rolling. b, venous leukocyte rolling and crawling with and against blood flow direction. c, Perivascular microglial process contact with intravascular cell. d, transendothelial migration and perivascular leukocyte accumulation. e, Mid tissue infiltrating leukocyte motility. f, Reverse migration of leukocyte into retinal vein. Scale bars=10 µm.

Figure 27:
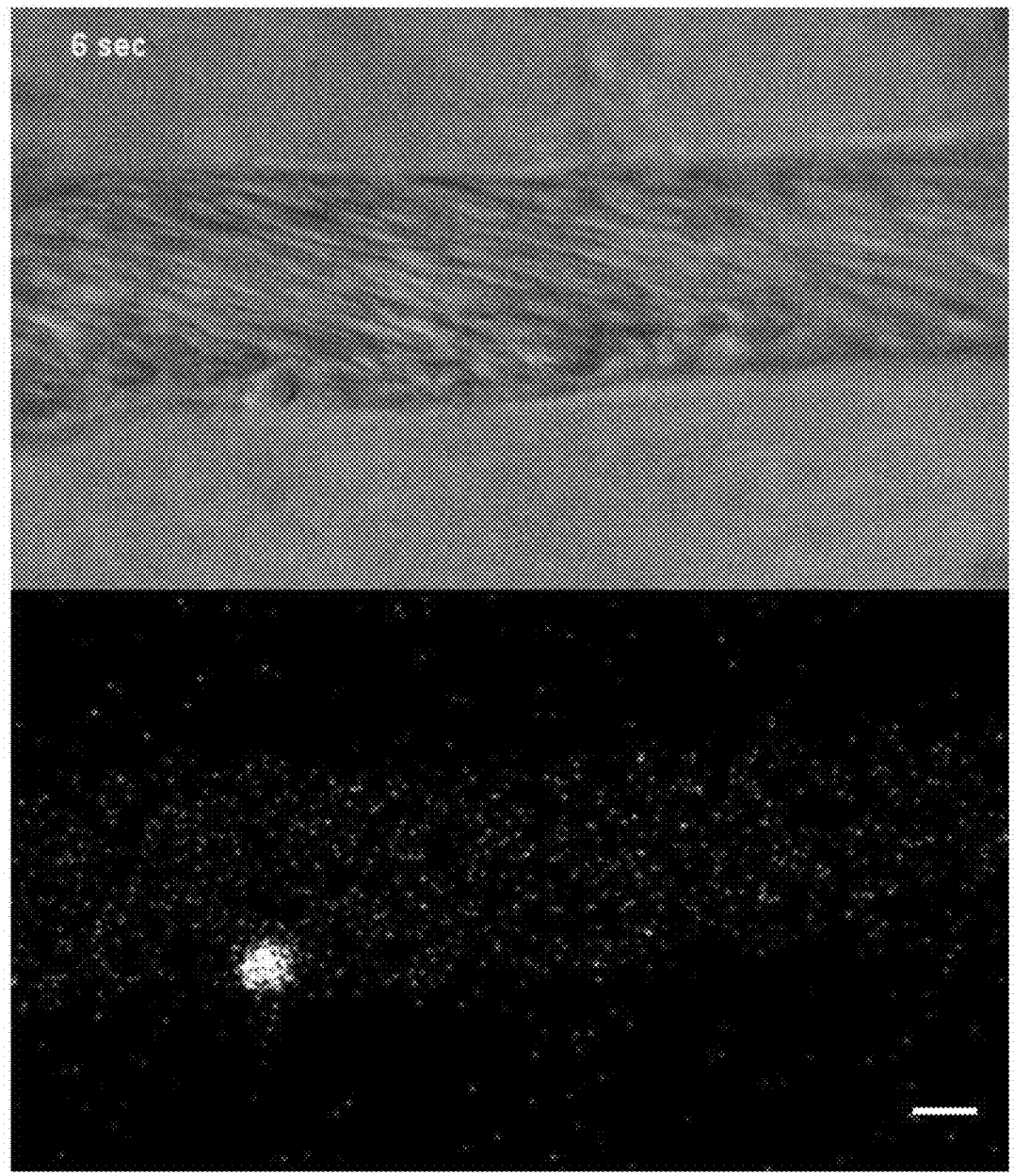
FIG. 27 is a series of still images representing a neutrophil rolling with label

FIG. 27 is a series of still images representing a neutrophil rolling with label; Extended Data Video 4. Neutrophil endothelial rolling within post-capillary venule with fluorescent labelling with anti-Ly6G antibody. Six hours post LPS. Simultaneous aligned acquisition of 796 nm reflectance (top) and anti-Ly6G conjugated AlexaFluor 647 fluorescence. Scale bar=10 µm.

FIG. 28 is a series of still images representing a video of microglia plus dynamic processes.

Figure 29:
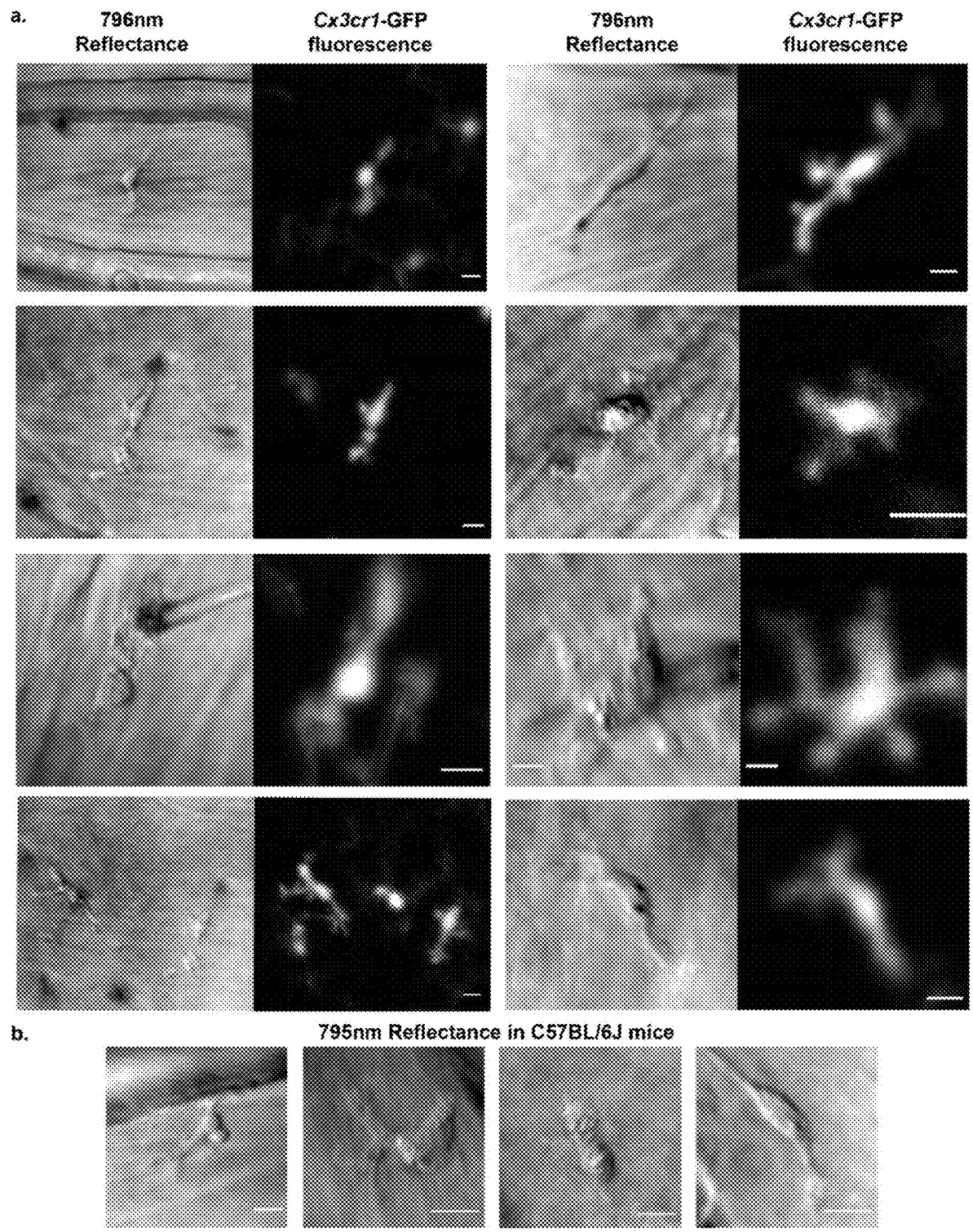
FIG. 29 is an extended data figure showing Microglia diversity.

FIG. 29 is an extended data figure showing Microglia diversity; Extended Data FIG. 1. Microglia are visible by reflectance imaging alone within the inner retina by AOSLO. a, 796 nm reflectance images alongside simultaneously acquired GFP fluorescence channel images in 6-week-old Cx3cr1GFP1+ mice (50 frame averaging), confirm these are inner retinal microglia. Sub-cellular features are visible in the reflectance channel. b, Representative reflectance images of C57BL/6J mice, demonstrating similar structures, as a control for GFP effects upon reflectance. Scale bars=10 µm.

Figure 30:
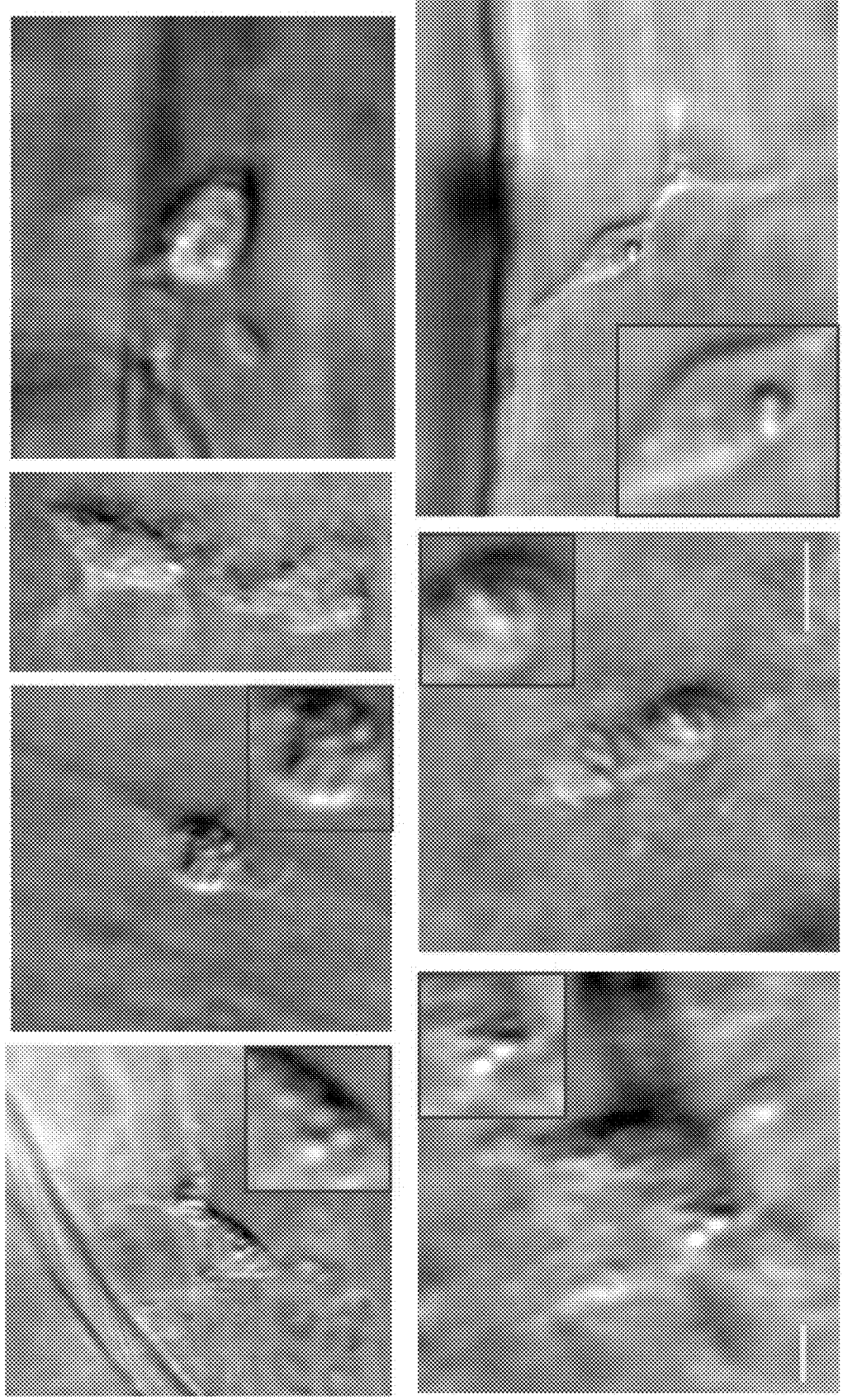
FIG. 30 is an extended data figure showing sub-cellular structures.

FIG. 30 is an extended data figure showing sub-cellular structures.

Figure 31:
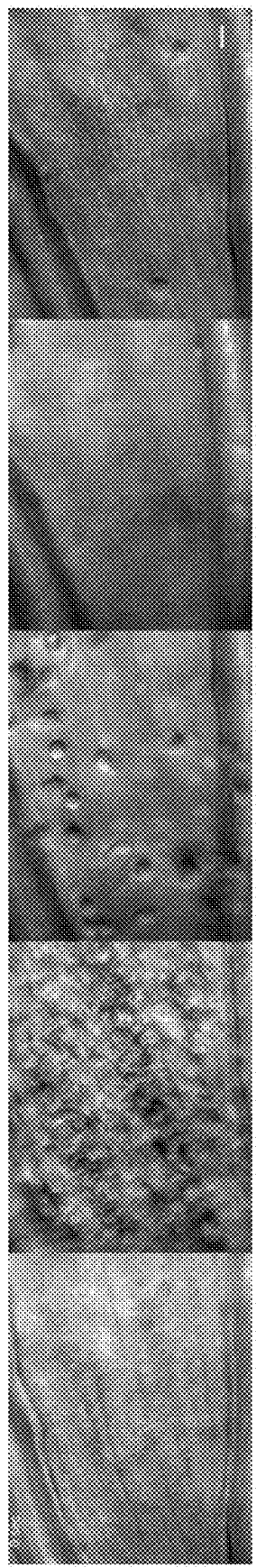
FIG. 31 is a series of still images representing a disease time course series evaluated with a U-Net.

FIG. 31 is a series of still images representing a time course video of a U-Net evaluation for FIG. 30.

Figure 32:
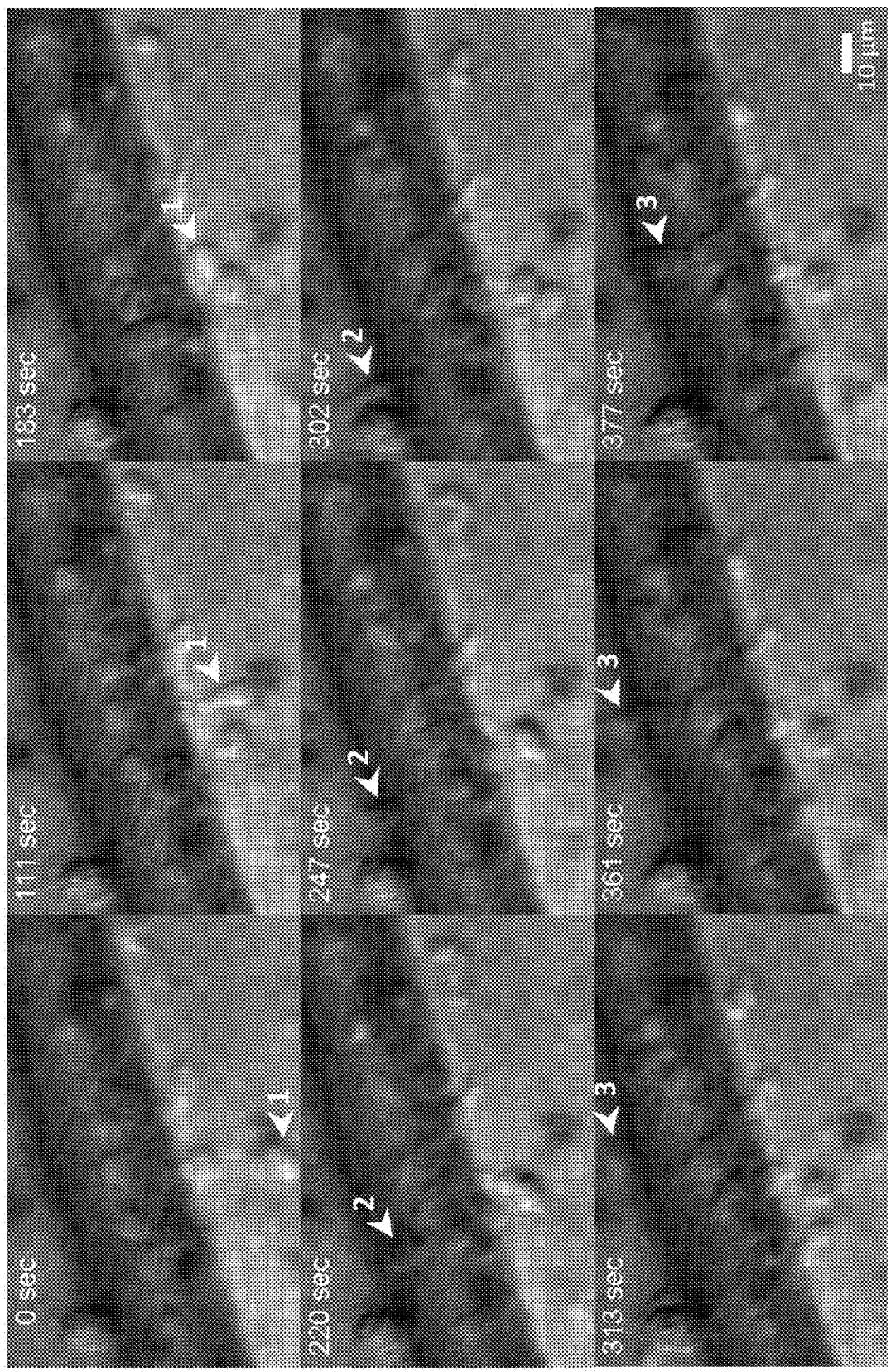
FIG. 32 is a series of images showing a AOSLO time-lapse sequence captured using the methods and configurations of the Application.

FIG. 32 is a series of images showing an AOSLO time-lapse sequence captured using the new methods and configurations of the Application. Each panel shows a unique snapshot of the immune cells surrounding a venule in the mouse retina. The timestamp of each snapshot is given in the top-left of each panel. The mouse has a local inflammation induced by intravitreal injection of lipopolysaccharide. The immune cells are clearly dynamic and motile. Every cell has its own story, performing an array of characteristic movements critical to the body's immune response. Here we point out a subset of the types of cell activity: The arrows marked '1' all point to the same immune cell as it migrates in the retinal tissue, outside the vessel. The arrows marked '2' all show another immune cell as it exits the vessel to fight infection—thereby crossing the blood-brain barrier, a process critical in immune response and drug delivery. The arrows marked '3' point to yet another immune cell which is re-entering the vessel, having completed its job of fighting the local inflammation outside.

REFERENCES for Part 4
1. Rosenbaum, J. et al. Imaging Ocular Immune Responses by Intravital Microscopy. Int Rev Immunol 21, 255-273 (2009).
2. Joseph, A., Guevara-Torres, A. & Schallek, J Imaging single-cell blood flow in the smallest to largest vessels in the living retina. Elife 8, e45077 (2019).
3. Marcos, S. et al. Vision science and adaptive optics, the state of the field. Vision Research 132, 3-33 (2017).
4. Chu, C. J. et al. Multimodal analysis of ocular inflammation using the endotoxin-induced uveitis mouse model. Disease Models and Mechanisms 9, 473-481 (2016).
5. Guevara-Torres, A., Joseph, A. & Schallek, J. Label free measurement of retinal blood cell flux, velocity, hematocrit and capillary width in the living mouse eye. Biomedical optics express 7, 4228-4249 (2016).
6. Marki, A., Buscher, K., Mikulski, Z., Pries, A. & Ley, K. Rolling neutrophils form tethers and slings under physiologic conditions in vivo. Journal of Leukocyte Biology 103, 67-70 (2018).
7. Uderhardt, S., Martins, A. J., Tsang, J. S., Lämmermann, T. & Germain, R. N. Resident Macrophages Cloak Tissue Microlesions to Prevent Neutrophil-Driven Inflammatory Damage. Cell 177, 541-555.e17 (2019).
8. Woodfin, A. et al. The junctional adhesion molecule JAM-C regulates polarized transendothelial migration of neutrophils in vivo. Nature immunology 12, 761-9 (2011).

Part 5—Exemplary Applications of Immune Cell Imaging Using the New Method and Configurations of the Application The new method and configurations of the Application can also be used for label-free and noninvasive in vivo imaging of immune cells in the retina both in a healthy condition and in a diseased condition. Current methods for assessing retinal immune health in humans include examination of ocular fundus images, which do not show either the structure or activity of the translucent immune cells (white blood cells, microglia and other types of immune cells). This is due to the limited resolution and contrast of current imaging techniques.

The new methods and configurations described hereinabove, which improve the observed contrast of translucent cells in the retina (in the absence of a contrast agent), enable visualization of immune cell activity in health and disease, including: leukocyte (white blood cell) rolling, leukocyte arrest, leukocyte trans-endothelial migration (extravasation), leukocyte re-entry into vessel following resolution of inflammation, microglial cell motility and leukocyte motility in retinal tissue. Video-rate (e.g. about 25 Hz) and time-lapse imaging of the immune cells show the dynamic behavior of both the complete cell (cell migration) and the movement of sub-cellular structures, all imaged label-free. Exemplary biomarkers that can be reported include immune cell-body migration velocity, immune cell process velocity, leukocyte rolling speed, immune cell count, immune cell area, immune cell migration path and direction vectors, and migration confinement ratio.

Due to the noninvasive nature and the use of safe levels of near-infrared or visible wavelengths of light, these new method and configurations offer improvements of utility in detection, diagnosis and assessment of treatment efficacy of inflammatory diseases of the human eye, such as, for example, posterior and anterior uveitis, diabetes, birdshot chorioretinopathy/uveitis, vasculitis and sarcoidosis.

Additionally, because of the current lack of techniques to visualize the activity of immune cells in the brain and other parts of the human body, the described method also has the utility of detection, diagnosis and assessment of treatment efficacy of any human disease that has an inflammatory component by viewing backscattered light from a screen behind the objects of interest, as described hereinabove. Moreover, the new methods and configurations, such as biomarkers of immune cell activity (e.g. biomarkers as described hereinabove), can be used to quantify the safety and treatment efficacy of drugs and other medication to treat inflammatory diseases.

Software and/or firmware to perform the new methods as described hereinabove can be provided on a computer readable non-transitory storage medium. A computer readable non-transitory storage medium as non-transitory data storage includes any data stored on any suitable media in a non-fleeting manner. Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method to image an in vivo object in an eye comprising:
    illuminating an object in the eye by a light source;
    configuring one or more detectors to receive light from a conjugate plane behind a confocal plane of said object, said conjugate plane acting as a light screen;
    receiving at said one or more detectors a backscattered light from said light source which has been refracted at least in part by said object before being backscattered from said light screen to provide a detector data; and
    processing said detector data over a time period by a computer to generate information about said object.

2. The method of claim 1, wherein said step of processing comprises processing said detector data over said time period by said computer to generate said information about said object as a two-dimensional image.

3. The method of claim 1, wherein said step of processing comprises processing said detector data over said time period by said computer to generate a type information about said object.

4. The method of claim 1, wherein said step of processing comprises processing said detector data over said time period by said computer to generate said information about an internal portion of said object.

5. The method of claim 1, wherein said step of illuminating said object comprises illuminating a cell, and said step of processing comprises processing said detector data over said time period by said computer to generate said information about a nucleus, nucleolus, or a heterochromatin of said cell.

6. The method of claim 1, wherein said step of illuminating said object comprises illuminating at least one red blood cell or at least one white blood cell.

7. The method of claim 1, wherein said step of illuminating said object comprises illuminating said object in an absence of a contrast agent or a label.

8. The method of claim 1, wherein said step of processing further comprises counting a number of red blood cells or a number of white blood cells in an imaged area.

9. The method of claim 1, wherein said step of processing comprises processing said detector data over said time period by said computer to generate said information about said object to diagnose a pathology or disease of an animal or human unrelated to the eye.

10. The method of claim 1, wherein said step of processing comprises processing said detector data over said time period by said computer to generate information about immune cell activity of an animal or human as viewed through the eye of the animal or the human.

11. The method of claim 1, wherein said step of processing comprises processing said detector data over said time period by said computer to generate said information in a 2D image which shows at least one of a white blood cell and a red blood cell.

12. The method of claim 1, wherein said step of processing comprises processing said detector data over said time period by said computer to generate said information in a 2D image which shows at least one of: leukocyte (white blood cell) rolling; leukocyte arrest; leukocyte trans-endothelial migration (extravasation); microglial cell motility; and leukocyte motility in a retinal tissue of an animal or human eye.

13. The method of claim 1, wherein said step of processing comprises processing said detector data over said time period by said computer to generate said information in a 2D image which shows a leukocyte re-entry into a vessel following resolution of inflammation.

14. The method of claim 1, wherein said step of processing comprises a object identification based on a ratiometric comparison of a forward scatter (FSC) detected light relative to a side scatter (SSC) detected light.

15. The method of claim 1, wherein said step of processing comprises a selective gating.

16. The method of claim 1, wherein said step of configuring, comprises configuring said one or more detectors to receive light from a surface of a layer of the eye acting as said light screen.

17. The method of claim 1, wherein said step of configuring, comprises configuring said one or more detectors to receive light from an internal portion of a layer of the eye acting as said light screen.

18. The method of claim 1, wherein said step of configuring, comprises configuring said one or more detectors for a split detection configuration.

19. The method of claim 1, wherein said step of processing comprises processing said detector data over a time period by a computer to generate images showing an immune cell migrating outside of a vessel of the eye, or an immune cell which is re-entering a vessel after fighting a local inflammation outside of the vessel.

20. The method of claim 19, performed in the absence of a contrast agent.

* * * * *